(12) United States Patent
Gugumus

(10) Patent No.: US 6,946,517 B2
(45) Date of Patent: Sep. 20, 2005

(54) STABILIZER MIXTURES

(75) Inventor: François Gugumus, Allschwil (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 177 days.

(21) Appl. No.: 10/278,154

(22) Filed: Oct. 22, 2002

(65) Prior Publication Data

US 2003/0153653 A1 Aug. 14, 2003

Related U.S. Application Data

(63) Continuation-in-part of application No. 09/639,293, filed on Aug. 15, 2000, now abandoned.

(30) Foreign Application Priority Data

Aug. 17, 1999 (EP) .............................................. 99810737

(51) Int. Cl.$^7$ .............................. C08K 3/22; C08K 5/34
(52) U.S. Cl. ........................... 524/847; 524/89; 524/99; 524/100; 524/102; 524/103; 524/413; 252/400.1; 252/401; 252/403
(58) Field of Search .............................. 252/400.1, 401, 252/403; 524/89, 99, 100, 102, 103, 413, 847

(56) References Cited

U.S. PATENT DOCUMENTS

| | | | | |
|---|---|---|---|---|
| 3,640,928 A | * | 2/1972 | Murayama et al. | 524/99 |
| 4,110,306 A | * | 8/1978 | Minagawa et al. | 524/102 |
| 4,198,334 A | * | 4/1980 | Rasberger | 524/102 |
| 4,233,412 A | * | 11/1980 | Rody et al. | 525/167 |
| 4,292,240 A | * | 9/1981 | Lai et al. | 540/492 |
| 4,340,534 A | * | 7/1982 | Wiezer et al. | 524/99 |
| 4,356,307 A | * | 10/1982 | Kelkenberg et al. | 546/200 |
| 4,408,051 A | * | 10/1983 | Hinsken et al. | 546/19 |
| 4,547,538 A | * | 10/1985 | Lai et al. | 524/100 |
| 4,619,958 A | * | 10/1986 | Haruna et al. | 524/102 |
| 4,689,416 A | * | 8/1987 | Ertl et al. | 546/19 |
| 4,769,457 A | * | 9/1988 | Helwig et al. | 544/180 |
| 4,863,981 A | * | 9/1989 | Gugumus | 524/97 |
| 4,929,652 A | | 5/1990 | Gugumus | 524/91 |
| 4,976,889 A | * | 12/1990 | Aumueller et al. | 252/403 |
| 5,026,849 A | * | 6/1991 | Kletecka et al. | 544/198 |
| 5,049,604 A | * | 9/1991 | Fujii et al. | 524/103 |
| 5,051,458 A | * | 9/1991 | Costanzi et al. | 524/99 |
| 5,071,981 A | * | 12/1991 | Son et al. | 544/198 |
| 5,182,390 A | * | 1/1993 | Sagawa et al. | 544/222 |
| 5,204,473 A | * | 4/1993 | Winter et al. | 546/188 |
| 5,393,812 A | | 2/1995 | Haley et al. | 524/100 |
| 5,679,733 A | * | 10/1997 | Malik et al. | 524/99 |
| 5,719,217 A | * | 2/1998 | Gugumus | 524/100 |
| 5,919,399 A | * | 7/1999 | Gugumus | 252/403 |
| 5,965,643 A | * | 10/1999 | Gugumus | 524/100 |
| 5,980,783 A | * | 11/1999 | Gugumus | 252/401 |
| 5,990,208 A | | 11/1999 | Andrews | 524/91 |
| 6,015,849 A | * | 1/2000 | Gugumus | 524/100 |
| 6,020,406 A | * | 2/2000 | Gugumus | 524/95 |
| 6,171,751 B1 | * | 1/2001 | Mourey et al. | 430/201 |

FOREIGN PATENT DOCUMENTS

| | | |
|---|---|---|
| EP | 0824137 | 2/1998 |
| EP | 1077227 | 2/2001 |
| GB | 2316409 | 2/1998 |
| WO | 97/05189 | 2/1997 |

OTHER PUBLICATIONS

N. S. Allen et al, Polym. Degrad. Stab. (1998), 61(1), pp. 139–149.

Derwent Abstract 49682W/30 and Chem. Abstr. 83:194519h (1975) for DE 2500314.

\* cited by examiner

Primary Examiner—Tae H. Yoon
(74) Attorney, Agent, or Firm—Shiela A. Loggins

(57) ABSTRACT

A stabilizer mixture containing
(A) for example a compound of the formula (A-I)

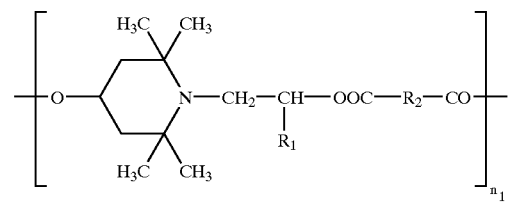

(A-I)

wherein $R_1$ is hydrogen or $C_1$–$C_4$alkyl, $R_2$ is a direct bond or $C_1$–$C_{10}$alkylene and $n_1$ is a number from 2 to 50;
(B) a sterically hindered amine compound; and
(C) anatase;
with the proviso that the component (B) is different from a compound of the formula (A-I).

10 Claims, No Drawings

STABILIZER MIXTURES

This is a continuation-in-part of Application Ser. No. 09/639,293 filed on Aug. 15, 2000, abandoned on Oct. 24, 2002.

The present invention relates to stabilizer mixtures containing one specific sterically hindered amine compound, a further hindered amine compound and anatase ($TiO_2$), the use of this mixture for stabilizing an organic material, in particular a synthetic polymer such as a polyolefin, against degradation induced by light, heat or oxidation and the organic material thus stabilized.

A stabilizer mixture containing two specific sterically hindered amine compounds and rutile ($TiO_2$) is for example known from U.S. Pat. No. 4,863,981. Stabilizer interactions in the thermal and photooxidation of titanium dioxide pigmented polypropylene films are described by N. S. Allen et al. in Polymer Degradation and Stability 61 (1998), 139–149.

The present invention relates in particular to a stabilizer mixture containing
(A) a compound of the formula (A-I)

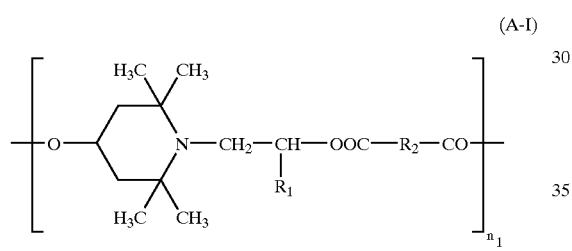

wherein $R_1$ is hydrogen or $C_1$–$C_4$alkyl, $R_2$ is a direct bond or $C_1$–$C_{10}$alkylene and $n_1$ is a number from 2 to 50; or at least one compound of the formulae (A-II-a) and (A-II-b)

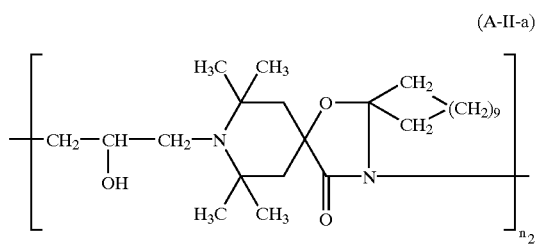

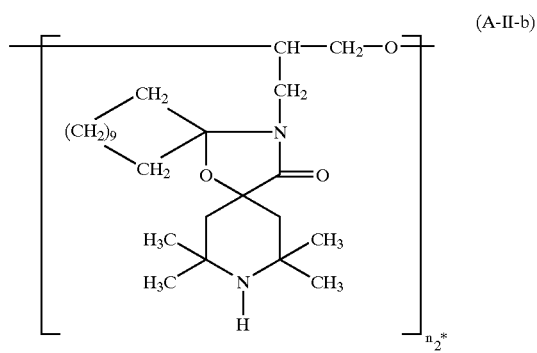

wherein $n_2$ and $n_2{}^*$ are a number from 2 to 50; or a compound of the formula (A-III)

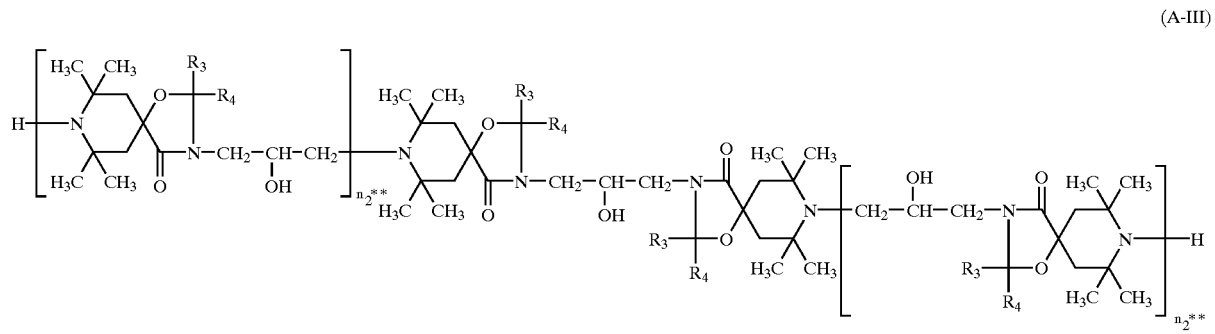

wherein $R_3$ and $R_4$ independently of one another are hydrogen or $C_1$–$C_8$alkyl, or $R_3$ and $R_4$ together form a $C_5$–$C_{11}$alkylene group, the variables $n_2$** are independently of one another a number from 1 to 50;

(B) a sterically hindered amine compound; and
(C) anatase;

with the proviso that the component (B) is different from a compound of the formula (A-I), (A-II-a), (A-II-b) and (A-III).

Examples of alkyl containing not more than 8 carbon atoms are methyl, ethyl, propyl, butyl, pentyl, hexyl, heptyl and octyl.

Examples of alkylene (straight-chain or branched) containing not more than 11 carbon atoms are methylene, ethylene, propylene, trimethylene, tetramethylene, pentamethylene, 3,3-pentanediyl, hexamethylene, octamethylene, decamethylene and undecamethylene. $R_2$ is preferably $C_2$–$C_5$alkylene.

$n_1$, $n_2$ and $n_2$* are preferably a number from 2 to 25, in particular 2 to 20 or 2 to 10.

$n_2$** is preferably a number from 1 to 25, in particular 1 to 20 or 1 to 10.

The definition of the terminal groups which saturate the free valences in the compounds of the formulae (A-I), (A-II-a) and (A-II-b) depend on the processes used for their preparation. The terminal groups can also be modified after the preparation of the compounds.

In the compounds of the formula (A-I), the terminal group bonded to the 2,2,6,6-tetramethyl-4-oxy-1-piperidyl radical is for example hydrogen or —CO—$R_2$—COOQ with Q being e.g. methyl, ethyl or propyl, and the terminal group bonded to the diacyl radical is for example —OQ or a group

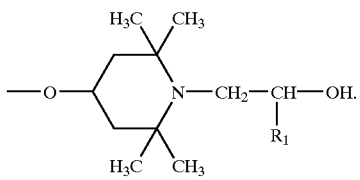

In the compounds of the formula (A-II-a), the terminal group bonded to the nitrogen can be, for example, hydrogen and the terminal group bonded to the 2-hydroxypropylene radical can be, for example, a

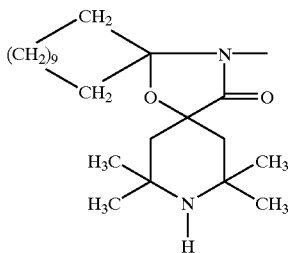

group.

In the compounds of the formula (A-II-b), the terminal group bonded to the dimethylene radical can be, for example, —OH, and the terminal group bonded to the oxygen can be, for example, hydrogen. The terminal groups can also be polyether radicals.

The component (A) is preferably a compound of the formula (A-I) with $R_1$ being hydrogen, $R_2$ being ethylene and n, being a number from 2 to 20; or at least one compound of the formulae (A-II-a) and (A-II-b) with $n_2$ and $n_2$* being a number from 2 to 20; or a compound of the formula (A-III) with the radicals $R_3$ and $R_4$ together forming undecamethylene and the variables $n_2$** independently of one another being a number from 1 to 20.

The component (A) is in particular a compound of the formula (A-I) with $R_1$ being hydrogen, $R_2$ being ethylene and no being a number from 2 to 20.

The compounds of components (A), (B) and (C) are known and most of them are commercially available.

Component (A) is in particular the commercially available product ®TINUVIN 622 or ®HOSTAVIN N 30. Compounds of the formula (A-III) are described in detail in WO-A-98/51690.

Component (B) is preferably a compound containing at least one group of the formula (I) or (II)

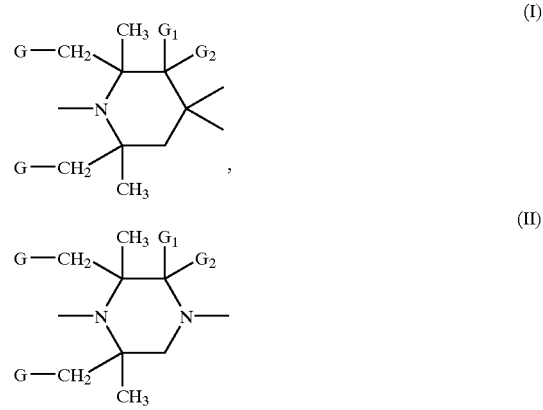

in which G is hydrogen or methyl, and
$G_1$ and $G_2$, independently of one another, are hydrogen, methyl or together are a substituent =O.

More detailed examples of sterically hindered amines are described below under classes (a') to (i').

(a') A compound of the formula (Ia)

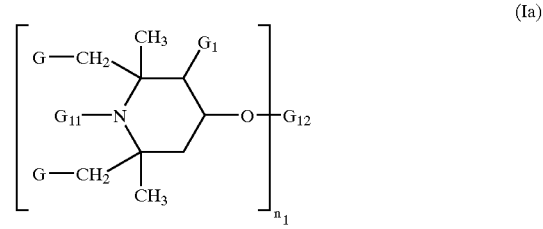

in which $n_1$ is a number from 1 to 4, G and $G_1$, independently of one another, are hydrogen or methyl, $G_{11}$ is hydrogen, O, hydroxyl, $C_1$–$C_{18}$alkyl, $C_3$–$C_8$alkenyl, $C_3$–$C_8$alkynyl, $C_7$–$C_{12}$aralkyl, $C_1$–$C_{18}$alkoxy, $C_5$–$C_8$cycloalkoxy, $C_7$–$C_9$phenylalkoxy, $C_1$–$C_8$alkanoyl, $C_3$–$C_5$alkenoyl, $C_1$–$C_{18}$alkanoyloxy, glycidyl or a group of the formula —$CH_2CH(OH)$—Z, in which Z is hydrogen, methyl or phenyl, $G_{11}$ preferably being H, $C_1$–$C_4$alkyl, allyl, benzyl, acetyl or acryloyl, and $G_{12}$, if $n_1$ is 1, is hydrogen, $C_1$–$C_{18}$alkyl which is uninterrupted or interrupted by one or more oxygen atoms, cyanoethyl, benzoyl, glycidyl, a monovalent radical of an aliphatic, cycloaliphatic, araliphatic, unsaturated or aromatic carboxylic acid, carbamic acid or phosphorus-containing acid or a monovalent silyl radical, preferably a radical of an aliphatic carboxylic acid having 2 to 18 carbon atoms, of a cycloaliphatic carboxylic acid having 7 to 15 carbon atoms, or an α,β-unsaturated carboxylic acid having 3 to 5 carbon atoms or of an aromatic carboxylic acid having 7 to 15 carbon atoms, where each carboxylic acid can be substituted in the aliphatic, cycloaliphatic or aromatic moiety by 1 to 3 —COOZ$_{12}$ groups, in which Z$_{12}$ is H, C$_1$–C$_{20}$alkyl, C$_3$–C$_{12}$alkenyl, C$_5$–C$_7$cycloalkyl, phenyl or benzyl, G$_{12}$, if n$_1$ is 2, is C$_2$–C$_{12}$alkylene, C$_4$–C$_{12}$alkenylene, xylylene, a divalent radical of an aliphatic, cycloaliphatic, araliphatic or aromatic dicarboxylic acid, dicarbamic acid or phosphorus-containing acid or a divalent silyl radical, preferably a radical of an aliphatic dicarboxylic acid having 2 to 36 carbon atoms, or a cycloaliphatic or aromatic dicarboxylic acid having 8–14 carbon atoms or of an aliphatic, cycloaliphatic or aromatic dicarbamic acid having 8–14 carbon atoms, where each dicarboxylic acid may be substituted in the aliphatic, cycloaliphatic or aromatic moiety by one or two —COOZ$_{12}$ groups, G$_{12}$, if n$_1$ is 3, is a trivalent radical of an aliphatic, cycloaliphatic or aromatic tricarboxylic acid, which may be substituted in the aliphatic, cycloaliphatic or aromatic moiety by
—COOZ$_{12}$, of an aromatic tricarbamic acid or of a phosphorus-containing acid, or is a trivalent silyl radical, and G$_{12}$, if n$_1$, is 4, is a tetravalent radical of an aliphatic, cycloaliphatic or aromatic tetracarboxylic acid.

The carboxylic acid radicals mentioned above are in each case taken to mean radicals of the formula (—CO)$_x$R, where x is as defined above for n$_1$, and the meaning of R arises from the definition given above.

Alkyl with up to 20 carbon atoms is, for example, methyl, ethyl, n-propyl, n-butyl, sec-butyl, tert-butyl, n-hexyl, n-octyl, 2-ethylhexyl, n-nonyl, n-decyl, n-undecyl, n-dodecyl, n-tridecyl, n-tetradecyl, n-hexadecyl or n-octadecyl.

C$_3$–C$_8$alkenyl G$_{11}$ can be, for example, 1-propenyl, allyl, methallyl, 2-butenyl, 2-pentenyl, 2-hexenyl, 2-octenyl, or 4-tert-butyl-2-butenyl.

C$_3$–C$_8$alkynyl G$_{11}$ is preferably propargyl.

C$_7$–C$_{12}$aralkyl G$_1$, is, in particular, phenethyl, especially benzyl.

C$_1$–C$_{18}$alkoxy G$_{11}$ is, for example, methoxy, ethoxy, propoxy, isopropoxy, butoxy, isobutoxy, pentoxy, isopentoxy, hexoxy, heptoxy, octoxy, decyloxy, dodecyloxy, tetradecyloxy, hexadecyloxy and octadecyloxy. C$_6$–C$_{12}$alkoxy, in particular heptoxy and octoxy, is preferred.

C$_5$–C$_8$cycloalkoxy G$_{11}$ is, for example, cyclopentoxy, cyclohexoxy, cycloheptoxy, cyclooctoxy, cyclodecyloxy and cyclododecyloxy. C$_5$–C$_8$cycloalkoxy, in particular cyclopentoxy and cyclohexoxy, is preferred.

C$_7$–C$_9$phenylalkoxy is, for example, benzyloxy.

C$_1$–C$_8$alkanoyl G$_{11}$ is, for example, formyl, propionyl, butyryl, octanoyl, but preferably acetyl and C$_3$–C$_5$alkenoyl G$_{11}$ is in particular acryloyl.

C$_1$–C$_{18}$alkanoyloxy G$_{11}$ is, for example, formyloxy, acetyloxy, propionyloxy, butyryloxy, valeryloxy, lauryloxy, palmitoyloxy and stearoyloxy.

Examples of several G$_{12}$ radicals are given below.

If G$_{12}$ is a monovalent radical of a carboxylic acid, it is, for example, an acetyl, caproyl, stearoyl, acryloyl, methacryloyl, benzoyl or β(3-(3,5-di-tert-butyl-4-hydroxyphenyl)propionyl radical.

If G$_{12}$ is a monovalent silyl radical, it is, for example, a radical of the formula —(C$_j$H$_{2j}$)—Si(Z')$_2$Z", in which j is an integer in the range from 2 to 5, and Z' and Z", independently of one another, are C$_1$–C$_4$alkyl or C$_1$–C$_4$alkoxy.

If G$_{12}$ is a divalent radical of a dicarboxylic acid, it is, for example, a malonyl, succinyl, glutaryl, adipoyl, suberoyl, sebacoyl, maleoyl, itaconyl, phthaloyl, dibutylmalonyl, dibenzylmalonyl, butyl(3,5-di-tert-butyl-4-hydroxybenzyl) malonyl or bicycloheptenedicarbonyl radical or a group of the formula

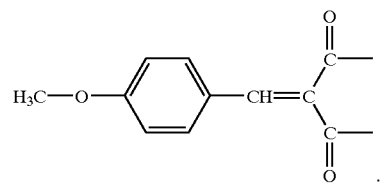

If G$_{12}$ is a trivalent radical of a tricarboxylic acid, it is, for example, a trimellitoyl, citryl or nitrilotriacetyl radical.

If G$_{12}$ is a tetravalent radical of a tetracarboxylic acid, it is, for example, the tetravalent radical of butane-1,2,3,4-tetracarboxylic acid or of pyromellitic acid.

If G$_{12}$ is a divalent radical of a dicarbamic acid, it is, for example, hexamethylenedicarbamoyl or 2,4-toluylenedicarbamoyl radical.

Preference is given to compounds of the formula (Ia) in which G and G$_1$ are hydrogen, G$_{11}$ is hydrogen or methyl, n$_1$ is 2 and G$_{12}$ is the diacyl radical of an aliphatic dicarboxylic acid having 4–12 carbon atoms.

Examples of polyalkylpiperidine compounds from this class are the following compounds:
1) 4-hydroxy-2,2,6,6-tetramethylpiperidine
2) 1-allyl-4-hydroxy-2,2,6,6-tetramethylpiperidine
3) 1-benzyl-4-hydroxy-2,2,6,6-tetramethylpiperidine
4) 1-(4-tert-butyl-2-butenyl)-4-hydroxy-2,2,6,6-tetramethylpiperidine
5) 4-stearoyloxy-2,2,6,6-tetramethylpiperidine
6) 1-ethyl-4-salicyloyloxy-2,2,6,6-tetramethylpiperidine
7) 4-methacryloyloxy-1,2,2,6,6-pentamethylpiperidine
8) 1,2,2,6,6-pentamethylpiperidin-4-yl β-(3,5-di-tert-butyl-4-hydroxyphenyl)propionate
9) di(1-benzyl-2,2,6,6-tetramethylpiperidin-4-yl) maleate
10) di(2,2,6,6-tetramethylpiperidin-4-yl)succinate
11) di(2,2,6,6-tetramethylpiperidin-4-yl)glutarate
12) di(2,2,6,6-tetramethylpiperidin-4-yl)adipate
13) di(2,2,6,6-tetramethylpiperidin-4-yl)sebacate
14) di(1,2,2,6,6-pentamethylpiperidin-4-yl)sebacate
15) di(1,2,3,6-tetramethyl-2,6-diethyl-piperidin-4-yl) sebacate
16) di(1-allyl-2,2,6,6-tetramethylpiperidin-4-yl)phthalate
17) 1-hydroxy-4-β-cyanoethoxy-2,2,6,6-tetramethylpiperidine
18) 1-acetyl-2,2,6,6-tetramethylpiperidin-4-yl acetate
19) tri(2,2,6,6-tetramethylpiperidin-4-yl)trimellitate
20) 1-acryloyl-4-benzyloxy-2,2,6,6-tetramethylpiperidine
21) di(2,2,6,6-tetramethylpiperidin-4-yl)diethylmalonate
22) di(1,2,2,6,6-pentamethylpiperidin-4-yl)dibutylmalonate
23) di(1,2,2,6,6-pentamethylpiperidin-4-yl) butyl(3,5-di-tert-butyl-4-hydroxybenzyl)malonate
24) di(1-octyloxy-2,2,6,6-tetramethylpiperidin-4-yl) sebacate
25) di(1-cyclohexyloxy-2,2,6,6-tetramethylpiperidin-4-yl) sebacate
26) hexane-1',6'-bis(4-carbamoyloxy-1-n-butyl-2,2,6,6-tetramethylpiperidine)
27) toluene-2',4'-bis-(4-carbamoyloxy-1-n-propyl-2,2,6,6-tetramethylpiperidine)
28) dimethylbis(2,2,6,6-tetramethylpiperidin-4-oxy)silane
29) phenyltris(2,2,6,6-tetramethylpiperidin-4-oxy)silane 30) tris(1-propyl-2,2,6,6-tetramethylpiperidin-4-yl) phosphite
30-a) tris(1-methyl-2,2,6,6-tetramethylpiperidin-4-yl) phosphite
31) tris(1-propyl-2,2,6,6-tetramethylpiperidin-4-yl) phosphate
32) phenyl bis(1,2,2,6,6-pentamethylpiperidin-4-yl) phosphonate
33) 4-hydroxy-1,2,2,6,6-pentamethylpiperidine
34) 4-hydroxy-N-hydroxyethyl-2,2,6,6-tetramethylpiperidine
35) 4-hydroxy-N-(2-hydroxypropyl)-2,2,6,6-tetramethylpiperidine
36) 1-glycidyl-4-hydroxy-2,2,6,6-tetramethylpiperidine
36-a-1) 1,2,3,4-tetrakis[2,2,6,6-tetramethylpiperidin-4-yloxycarbonyl]butane
36-a-2) bis[2,2,6,6-tetramethylpiperidin-4-yloxycarbonyl]-bis[tridecyloxycarbonyl]butane
36-b-1) 1,2,3,4-tetrakis[1,2,2,6,6-pentamethylpiperidin-4-yloxycarbonyl]butane
36-b-2) bis[1,2,2,6,6-pentamethylpiperidin-4-yloxycarbonyl]-bis[tridecyloxycarbonyl]butane
36-c) 2,2,6,6-tetramethylpiperidin-4-yloxycarbonyl ($C_{15}$–$C_{17}$alkane)

36-d)

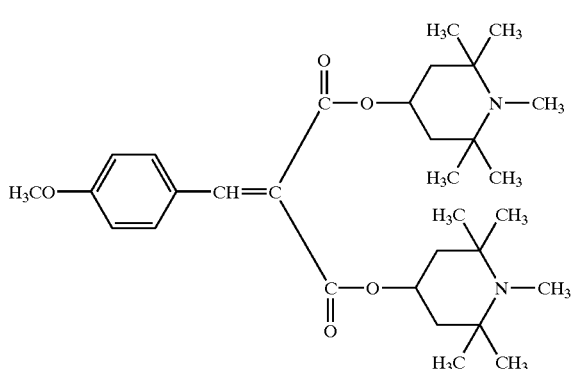

36-e)

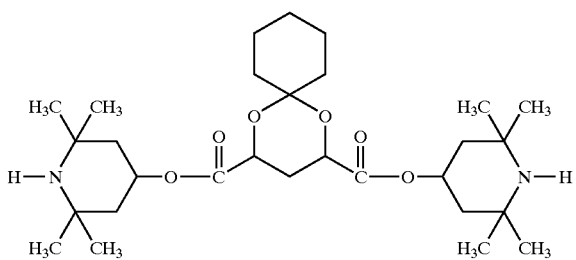

(b') A compound of the formula (Ib)

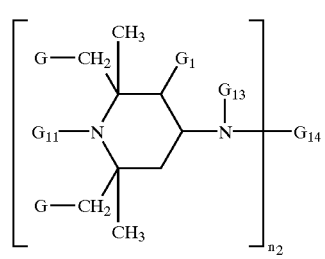
(Ib)

in which $n_2$ is the number 1, 2 or 3, G, $G_1$ and $G_{11}$ are as defined under (a'), $G_{13}$ is hydrogen, $C_1$–$C_{12}$alkyl, $C_2$–$C_5$hydroxyalkyl, $C_5$–$C_7$cycloalkyl, $C_7$–$C_8$aralkyl, $C_1$–$C_{18}$alkanoyl, $C_3$–$C_5$alkenoyl, benzoyl or a group of the formula

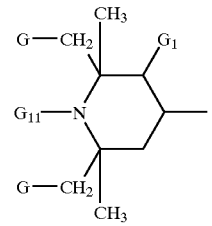

and $G_{14}$, if $n_2$ is 1, is hydrogen, $C_1$–$C_{18}$alkyl, $C_3$–$C_8$alkenyl, $C_5$–$C_7$cycloalkyl, $C_1$–$C_4$alkyl which is substituted by a hydroxyl, cyano, alkoxycarbonyl or carbamide group, glycidyl, a group of the formula —$CH_2$—CH(OH)—Z or of the formula —CONH—Z, in which Z is hydrogen, methyl or phenyl;

$G_{14}$, if $n_2$ is 2, is $C_2$–$C_{12}$alkylene, $C_6$–$C_{12}$arylene, xylylene, a —$CH_2$—CH(OH)—$CH_2$ group or a —$CH_2$—CH(OH)—$CH_2$—O—D—O— group, in which D is $C_2$–$C_{10}$alkylene, $C_6$–$C_{15}$arylene, $C_6$–$C_{12}$cycloalkylene, or, provided that $G_{13}$ is not alkanoyl, alkenoyl or benzoyl, $G_{14}$ can alternatively be 1-oxo-$C_2$–$C_{12}$alkylene, a divalent radical of an aliphatic, cycloaliphatic or aromatic dicarboxylic acid or dicarbamic acid or alternatively the group —CO—, $G_{14}$, if $n_2$ is 3, is a group

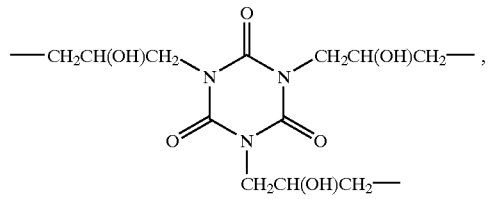

or, if $n_2$ is 1, $G_{13}$ and $G_{14}$ together can be the divalent radical of an aliphatic, cycloaliphatic or aromatic 1,2- or 1,3-dicarboxylic acid.

Some examples for the radicals $G_{13}$, $G_{14}$ and D are given below.

Any alkyl substituents are as defined above for (a').

Any $C_5$–$C_7$cycloalkyl substituents are, in particular, cyclohexyl.

$C_7$–$C_8$aralkyl $G_{13}$ is, in particular, phenylethyl or especially benzyl.

$C_2$–$C_5$hydroxyalkyl $G_{13}$ is, in particular, 2-hydroxyethyl or 2-hydroxypropyl.

$C_1$–$C_{18}$alkanoyl $G_{13}$ is, for example, formyl, acetyl, propionyl, butyryl, octanoyl, dodecanoyl, hexadecanoyl, octadecanoyl, but preferably acetyl, and $C_3$–$C_5$alkenoyl $G_{13}$ is, in particular, acryloyl.

$C_2$–$C_8$alkenyl $G_{14}$ is, for example, allyl, methallyl, 2-butenyl, 2-pentenyl, 2-hexenyl or 2-octenyl.

$G_{14}$ as a hydroxyl-, cyano-, alkoxycarbonyl- or carbamide-substituted $C_1$–$C_4$alkyl can be, for example, 2-hydroxyethyl, 2-hydroxypropyl, 2-cyanoethyl, methoxycarbonylmethyl, 2-ethoxycarbonylethyl, 2-aminocarbonylpropyl or 2-(dimethylaminocarbonyl)ethyl.

Any $C_2$–$C_{12}$alkylene radicals are, for example, ethylene, propylene, 2,2-dimethylpropylene, tetramethylene, hexamethylene, octamethylene, decamethylene or dodecamethylene.

Any $C_6$–$C_{15}$arylene substituents are, for example, o-, m- or p-phenylene, 1,4-naphthylene or 4,4'-diphenylene.

$C_6$–$C_{12}$cycloalkylene is, in particular, cyclohexylene.

$G_{14}$ as 1-oxo-$C_2$–$C_{12}$alkylene is preferably a group

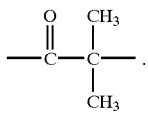

Preference is given to compounds of the formula (Ib) in which $n_2$ is 1 or 2, G and $G_1$ are hydrogen, $G_1$, is hydrogen or methyl, $G_{13}$ is hydrogen, $C_1$–$C_{12}$alkyl or a group of the formula

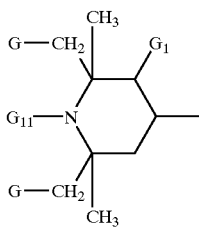

and $G_{14}$, in the case where n=1, is hydrogen or $C_1$–$C_{12}$alkyl, and, in the case where n=2, is $C_2$–$C_8$alkylene or 1-oxo-$C_2$–$C_8$alkylene.

Examples of polyalkylpiperidine compounds from this class are the following compounds:

37) N,N'-bis(2,2,6,6-tetramethylpiperidin-4-yl)hexamethylene-1,6-diamine
38) N,N'-bis(2,2,6,6-tetramethylpiperidin-4-yl)hexamethylene-1,6-diacetamide
39) bis(2,2,6,6-tetramethylpiperidin-4-yl)amine
40) 4-benzoylamino-2,2,6,6-tetramethylpiperidine
41) N,N'-bis(2,2,6,6-tetramethylpiperidin-4-yl)-N,N'-dibutyladipamide
42) N,N'-bis(2,2,6,6-tetramethylpiperidin-4-yl)-N,N'-dicyclohexyl-2-hydroxypropylene-1,3-diamine
43) N,N'-bis(2,2,6,6-tetramethylpiperidin-4-yl)-p-xylylenediamine
44) N,N'-bis(2,2,6,6-tetramethylpiperidin-4-yl)succinamide
45) bis(2,2,6,6-tetramethylpiperidin-4-yl) N-(2,2,6,6-tetramethylpiperidin-4-yl)-β-aminodipropionate
46) The compound of the formula

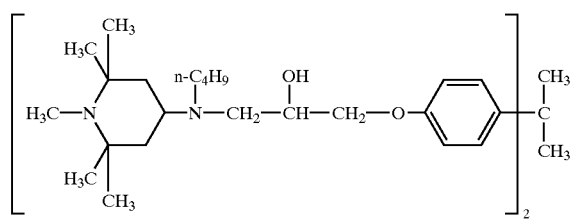

47) 4-(bis-2-hydroxyethylamino)-1,2,2,6,6-pentamethylpiperidine
48) 4-(3-methyl-4-hydroxy-5-tert-butyl-benzamido)-2,2,6,6-tetramethylpiperidine
49) 4-methacrylamido-1,2,2,6,6-pentamethylpiperidine

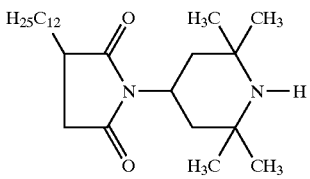

49-a-1)

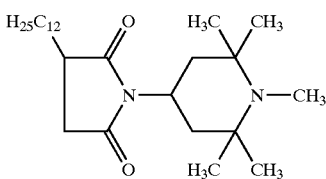

49-a-2)

49-b) N,N',N''-tris[2,2,6,6-tetramethylpiperidin-4-ylamino(2-hydroxypropylene)]isocyanurate
49-c) 2-(2,2,6,6-tetramethylpiperidin-4-ylamino)-2-(2,2,6,6-tetramethylpiperidin-4-ylaminocarbonyl)propane
49-d) 1,6-bis[N-(2,2,6,6-tetramethylpiperidin-4-yl)formylamino]hexane

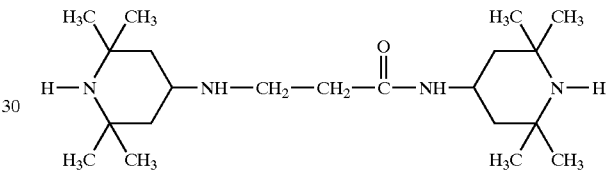

49-e)

(c') A compound of the formula (Ic)

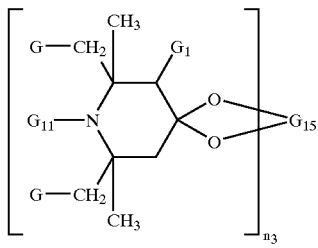

(Ic)

in which $n_3$ is the number 1 or 2, G, $G_1$ and $G_{11}$ are as defined under (a'), and $G_{15}$, if $n_3$ is 1, is $C_2$–$C_8$alkylene, $C_2$–$C_8$hydroxyalkylene or $C_4$–$C_{22}$acyloxyalkylene, and if $n_3$ is 2, $G_{15}$ is the (—$CH_2$)$_2$C($CH_2$—)$_2$ group.

$C_2$–$C_8$alkylene or $C_2$–$C_8$hydroxyalkylene $G_{15}$ is, for example, ethylene, 1-methylethylene, propylene, 2-ethylpropylene or 2-ethyl-2-hydroxymethylpropylene.

$C_4$–$C_{22}$acyloxyalkylene $G_{15}$ is, for example, 2-ethyl-2-acetoxymethylpropylene.

Examples of polyalkylpiperidine compounds from this class are the following compounds:

50) 9-aza-8,8,10,10-tetramethyl-1,5-dioxaspiro[5.5]undecane
51) 9-aza-8,8,10,10-tetramethyl-3-ethyl-1,5-dioxaspiro[5.5]undecane
52) 8-aza-2,7,7,8,9,9-hexamethyl-1,4-dioxaspiro[4.5]decane
53) 9-aza-3-hydroxymethyl-3-ethyl-8,8,9,10,10-pentamethyl-1,5-dioxaspiro[5.5]undecane 54) 9-aza-3-ethyl-3-acetoxymethyl-9-acetyl-8,8,10,10-tetramethyl-1,5-dioxaspiro[5.5]-undecane
55) 2,2,6,6-tetramethylpiperidine-4-spiro-2'-(1',3'-dioxane)-5'-spiro-5"-(1",3"-dioxane)-2"-spiro-4'"-(2'",2'",6'",6'"-tetramethylpiperidine)

(d') A compound of the formula (Id-1), (Id-2) or (Id-3),

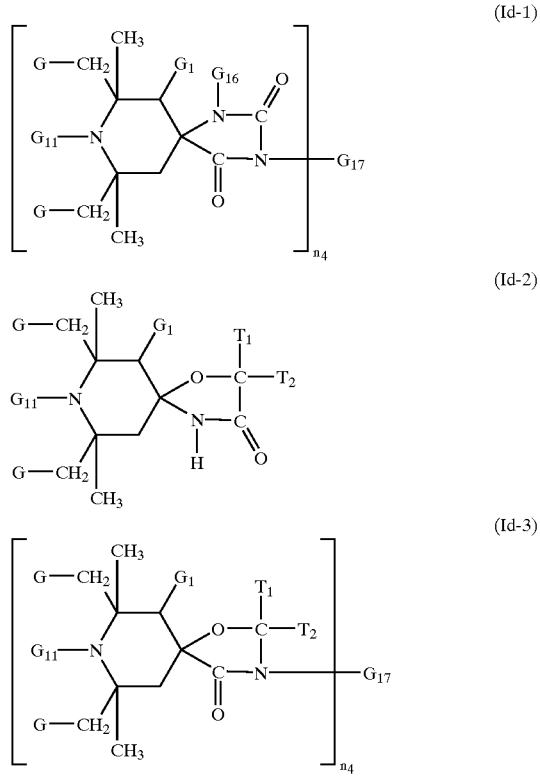

in which $n_4$ is the number 1 or 2, G, $G_1$ and $G_{11}$ are as defined under (a'), $G_{16}$ is hydrogen, $C_1$–$C_{12}$alkyl, allyl, benzyl, glycidyl or $C_2$–$C_6$alkoxyalkyl, and $G_{17}$, if $n_4$ is 1, is hydrogen, $C_1$–$C_{12}$alkyl, $C_3$–$C_5$alkenyl, $C_7$–$C_9$aralkyl, $C_5$–$C_7$cycloalkyl, $C_2$–$C_4$hydroxyalkyl, $C_2$–$C_6$alkoxyalkyl, $C_6$–$C_{10}$aryl, glycidyl or a group of the formula —$(CH_2)_p$—COO—Q or —$(CH_2)_p$—O—CO—Q, in which p is 1 or 2, and Q is $C_1$–$C_4$alkyl or phenyl, and $G_{17}$, if $n_4$ is 2, is $C_2$–$C_{12}$alkylene, $C_4$–$C_{12}$alkenylene, $C_6$–$C_{12}$arylene, a group of the formula —$CH_2$—CH(OH)—$CH_2$—O—D'—O—$CH_2$—CH(OH)—$CH_2$—, in which D' is $C_2$–$C_{10}$alkylene, $C_6$–$C_{15}$arylene or $C_6$–$C_{12}$cycloalkylene, or a group of the formula —$CH_2CH(OD")CH_2$—$(OCH_2$—$CH(OD")CH_2)_2$—, in which D" is hydrogen, $C_1$–$C_{18}$alkyl, allyl, benzyl, $C_2$–$C_{12}$alkanoyl or benzoyl, $T_1$ and $T_2$, independently of one another, are hydrogen, $C_1$–$C_{18}$alkyl or unsubstituted or halogen- or $C_1$–$C_4$alkyl-substituted $C_6$–$C_{10}$aryl or $C_7$–$C_9$aralkyl, or $T_1$ and $T_2$ together with the carbon atom bonding them form a $C_5$–$C_{14}$cycloalkane ring.

A compound of the formula (Id-3) is preferred.

Some examples of the several variables in the formulae (Id-1), (Id-2) and (Id-3) are given below.

Any $C_1$–$C_{12}$alkyl substituents are, for example, methyl, ethyl, n-propyl, n-butyl, sec-butyl, tert-butyl, n-hexyl, n-octyl, 2-ethylhexyl, n-nonyl, n-decyl, n-undecyl or n-dodecyl.

Any $C_1$–$C_{18}$alkyl substituents can be, for example, the abovementioned groups and in addition, for example, n-tridecyl, n-tetradecyl, n-hexadecyl or n-octadecyl.

Any $C_2$–$C_6$alkoxyalkyl substituents are, for example, methoxymethyl, ethoxymethyl, propoxymethyl, tert-butoxymethyl, ethoxyethyl, ethoxypropyl, n-butoxyethyl, tert-butoxyethyl, isopropoxyethyl or propoxypropyl.

$C_3$–$C_5$alkenyl $G_{17}$ is, for example, 1-propenyl, allyl, methallyl, 2-butenyl or 2-pentenyl.

$C_7$–$C_9$aralkyl $G_{17}$, $T_1$ and $T_2$ are, in particular, phenethyl or especially benzyl. If $T_1$ and $T_2$ together with the carbon atom form a cycloalkane ring, this can be, for example, a cyclopentane, cyclohexane, cyclooctane or cyclododecane ring.

$C_2$–$C_4$hydroxyalkyl $G_{17}$ is, for example, 2-hydroxyethyl, 2-hydroxypropyl, 2-hydroxybutyl or 4-hydroxybutyl.

$C_6$–$C_{10}$aryl $G_{17}$, $T_1$ and $T_2$ are, in particular, phenyl or α- or β-naphthyl, which are unsubstituted or substituted by halogen or $C_1$–$C_4$alkyl.

$C_2$–$C_{12}$alkylene $G_{17}$ is, for example, ethylene, propylene, 2,2-dimethylpropylene, tetramethylene, hexamethylene, octamethylene, decamethylene or dodecamethylene.

$C_4$–$C_{12}$alkenylene $G_{17}$ is, in particular, 2-butenylene, 2-pentenylene or 3-hexenylene.

$C_6$–$C_{12}$arylene $G_{17}$ is, for example, o-, m- or p-phenylene, 1,4-naphthylene or 4,4'-diphenylene.

$C_2$–$C_{12}$alkanoyl D" is, for example, propionyl, butyryl, octanoyl, dodecanoyl, but preferably acetyl.

$C_2$–$C_{10}$alkylene, $C_6$–$C_{15}$arylene or $C_6$–$C_{12}$cycloalkylene D' have, for example, one of the definitions given for D under (b').

Examples of polyalkylpiperidine compounds from this class are the following compounds:

56) 3-benzyl-1,3,8-triaza-7,7,9,9-tetramethylspiro[4.5]decane-2,4-dione
57) 3-n-octyl-1,3,8-triaza-7,7,9,9-tetramethylspiro[4.5]decane-2,4-dione
58) 3-allyl-1,3,8-triaza-1,7,7,9,9-pentamethylspiro[4.5]decane-2,4-dione
59) 3-glycidyl-1,3,8-triaza-7,7,8,9,9-pentamethylspiro[4.5]decane-2,4-dione
60) 1,3,7,7,8,9,9-heptamethyl-1,3,8-triazaspiro[4.5]decane-2,4-dione
61) 2-isopropyl-7,7,9,9-tetramethyl-1-oxa-3,8-diaza-4-oxospiro[4.5]decane
62) 2,2-dibutyl-7,7,9,9-tetramethyl-1-oxa-3,8-diaza-4-oxospiro[4.5]decane
63) 2,2,4,4-tetramethyl-7-oxa-3,20-diaza-21-oxodispiro[5.1.11.2]heneicosane
64) 2-butyl-7,7,9,9-tetramethyl-1 oxa-4,8-diaza-3-oxospiro[4.5]decane and preferably:
65) 8-acetyl-3-dodecyl-1,3,8-triaza-7,7,9,9-tetramethylspiro[4.5]decane-2,4-dione and the compounds of the following formulae:

66)

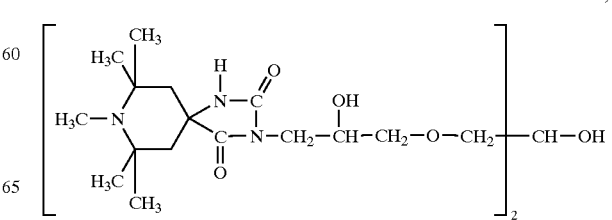

-continued

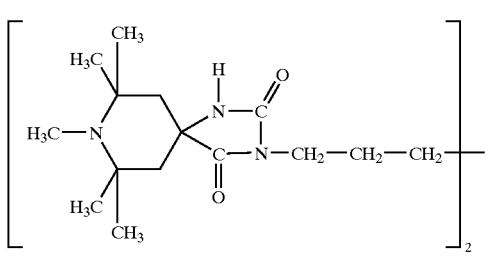
(67)

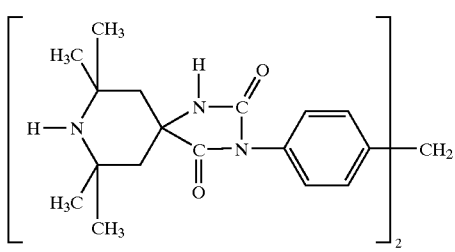
(68)

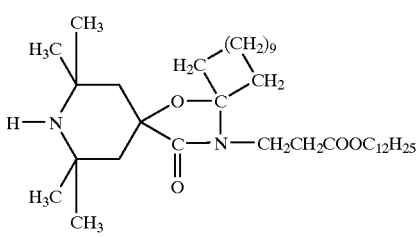
(69-a)

Mixture of 60% by weight of

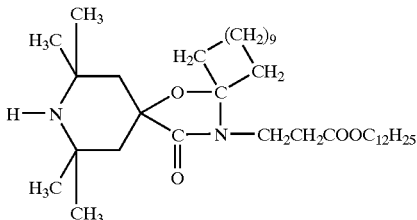

and 40% by weight of

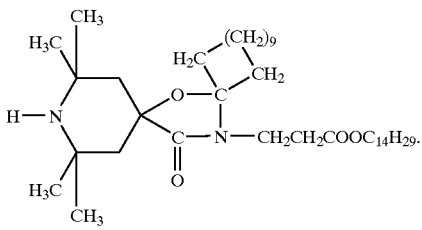
(69-b)

(e') A compound of the formula (Ie)

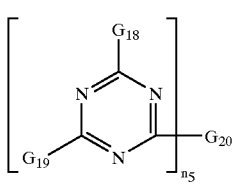
(Ie)

in which $n_5$ is the number 1 or 2, and $G_{18}$ is a group of the formula

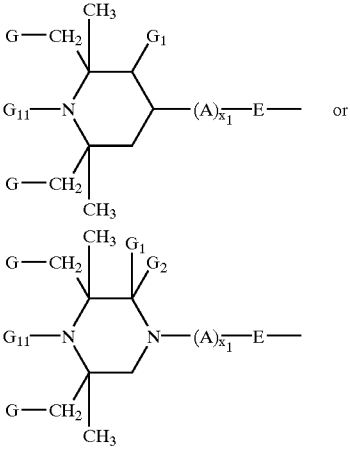

in which G and $G_{11}$ are as defined under (a'), and $G_1$ and $G_2$ are hydrogen, methyl or, together, are a substituent =O,
E is —O— or —ND'"—,
A is $C_2$–$C_6$alkylene or —(CH$_2$)$_3$—O— and
$x_1$ is the number 0 or 1,
D'" is hydrogen, $C_1$–$C_{12}$alkyl, $C_2$–$C_5$hydroxyalkyl or $C_5$–$C_7$cycloalkyl,
$G_{19}$ is identical to $G_{18}$ or is one of the groups —N($G_{21}$)($G_{22}$), —OG$_{23}$, —N(H)(CH$_2$OG$_{23}$) or —N(CH$_2$OG$_{23}$)$_2$,
$G_{20}$, if $n_5$=1, is identical to $G_{18}$ or $G_{19}$ and, if $n_5$=2, is an —E—D$^{IV}$—E— group, in which D$^{IV}$ is $C_2$–$C_8$alkylene or $C_2$–$C_8$alkylene which is interrupted by 1 or 2 —NG$_{21}$— groups,
$G_{21}$ is $C_1$–$C_{12}$alkyl, cyclohexyl, benzyl or $C_1$–$C_4$-hydroxyalkyl or a group of the formula

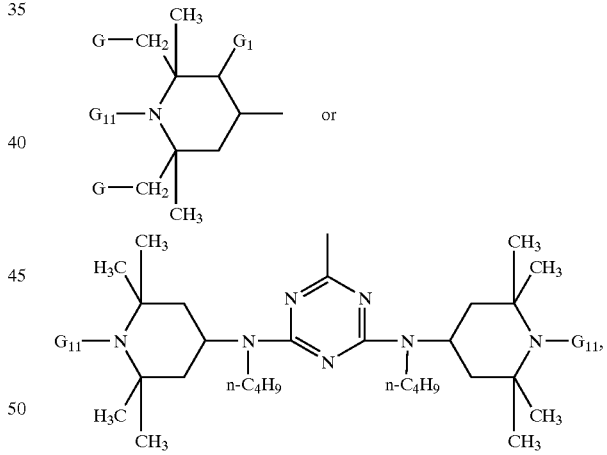

$G_{22}$ is $C_1$–$C_{12}$alkyl, cyclohexyl, benzyl or $C_1$–$C_4$hydroxyalkyl, and
$G_{23}$ is hydrogen, $C_1$–$C_{12}$alkyl or phenyl, or $G_{21}$ and $G_{22}$ together are $C_4$–$C_5$alkylene or $C_4$–$C_5$oxaalkylene, for example —CH$_2$CH$_2$—O—CH$_2$CH$_2$—, or a group of the formula —CH$_2$CH$_2$—N($G_{11}$)—CH$_2$CH$_2$—.

Some examples of the several variables in the formula (Ie) are given below.

Any $C_1$–$C_{12}$alkyl substituents are, for example, methyl, ethyl, n-propyl, n-butyl, sec-butyl, tert-butyl, n-hexyl, n-octyl, 2-ethylhexyl, n-nonyl, n-decyl, n-undecyl or n-dodecyl.

Any hydroxyalkyl substituents are, for example, 2-hydroxyethyl, 2-hydroxypropyl, 3-hydroxypropyl, 2-hydroxybutyl or 4-hydroxybutyl.

Any $C_5$–$C_7$cycloalkyl substituents are, for example, cyclopentyl, cyclohexyl or cycloheptyl. Cyclohexyl is preferred.

$C_2$–$C_6$alkylene A is, for example, ethylene, propylene, 2,2-dimethylpropylene, tetramethylene or hexamethylene.

If $G_2$, and $G_{22}$ together are $C_4$–$C_5$alkylene or oxaalkylene, they are, for example, tetramethylene, pentamethylene or 3-oxapentamethylene.

Examples of polyalkylpiperidine compounds from this class are the compounds of the following formulae:

70)
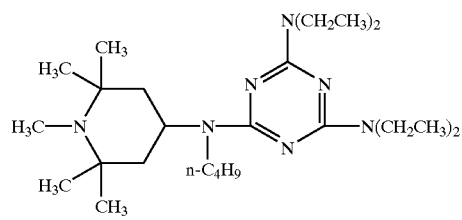

71)
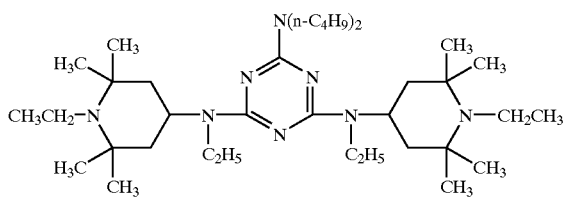

72)
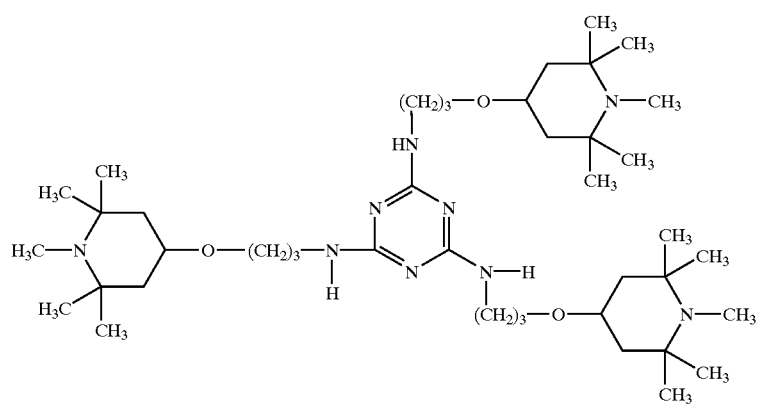

73)
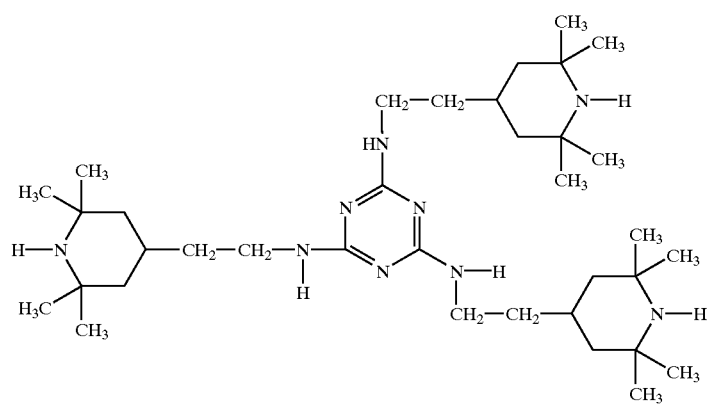

74)
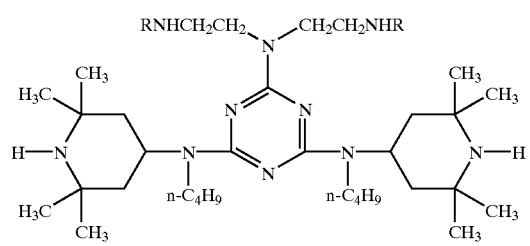

where R is
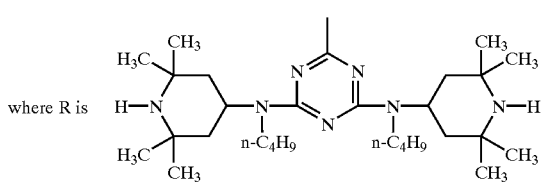

75)
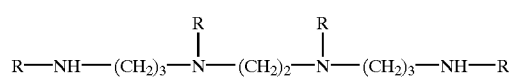

where R has the same meaning as in compound 74.
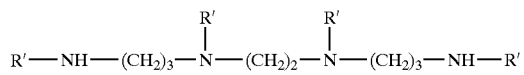
where R' is
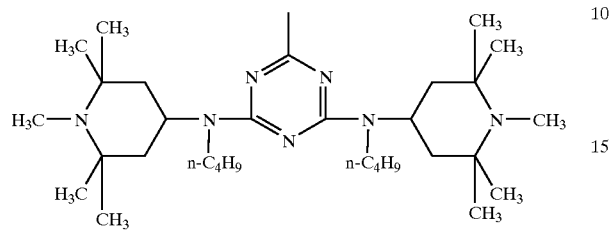
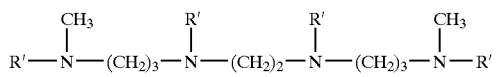
where R' has the same meaning as in compound 76.
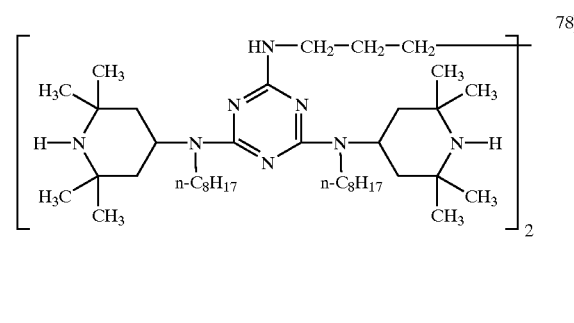
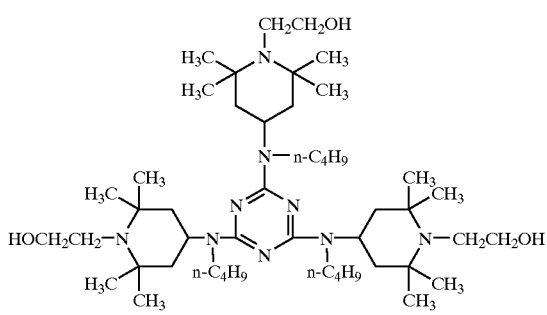
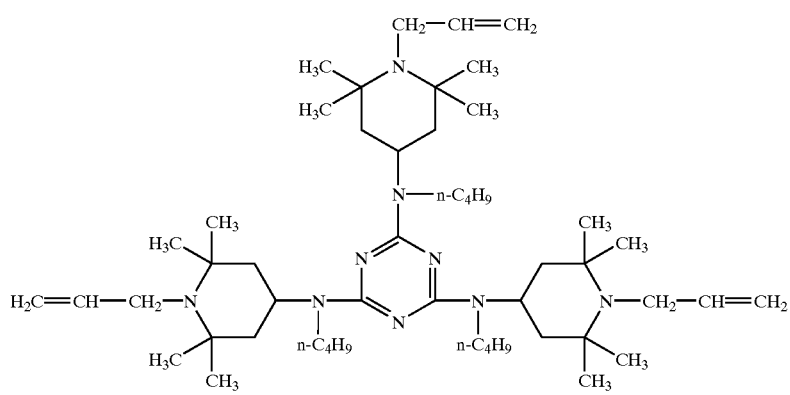

81)

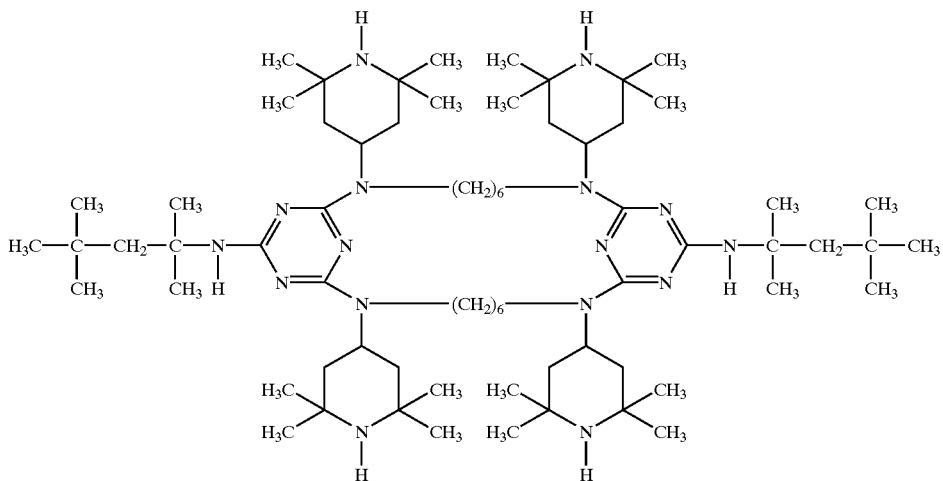

(f') A compound of the formula (If)

(If)

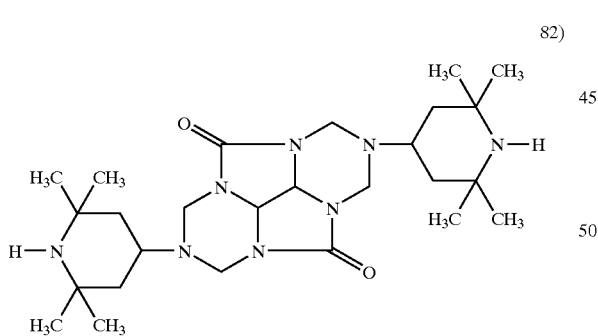

wherein $G_{11}$ is as defined under (a').

A preferred example from this class is the following compound:

82)

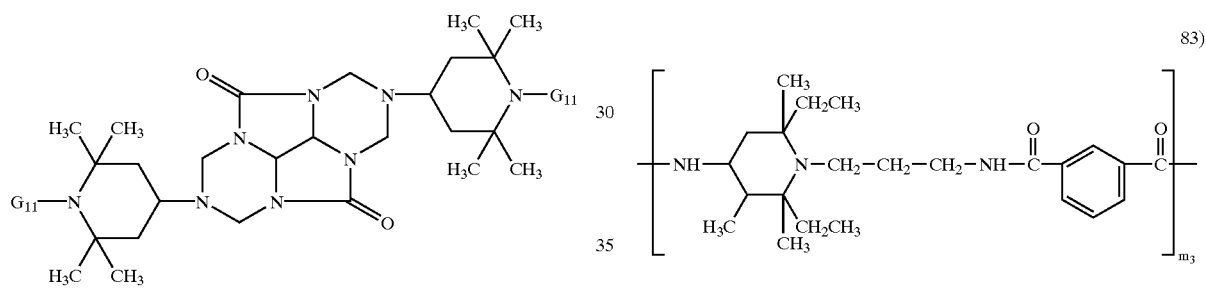

(g') Oligomeric or polymeric compounds whose recurring structural unit contains a 2,2,6,6-tetraalkylpiperidinyl radical, in particular polyesters, polyethers, polyamides, polyamines, polyurethanes, polyureas, polyaminotriazines, poly(meth)acrylates, poly(meth)acrylamides and copolymers thereof which contain such radicals.

Examples of 2,2,6,6-polyalkylpiperidine compounds from this class are the compounds of the following formulae. $m_3$ to $m_{14}$ is a number from 2 to about 200, preferably 2 to 100, for example 2 to 50, 2 to 40, 3 to 40 or 4 to 10.

The meanings of the end groups which saturate the free valences in the oligomeric or polymeric compounds listed below depend on the processes used for the preparation of said compounds. The end groups can also in addition be modified after the synthesis of the compounds.

83)

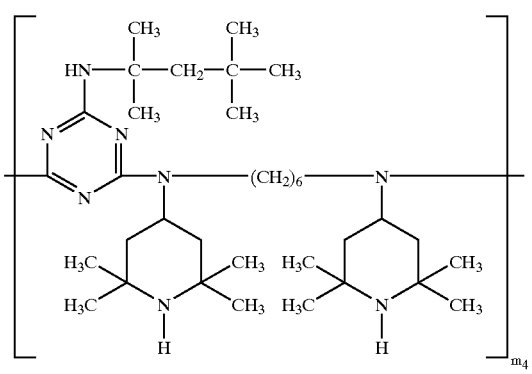

In the compound 83, the end group bonded to the amino residue can be, for example, a group

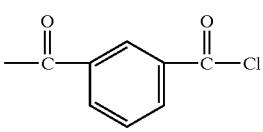

and the end group bonded to the diacyl residue can be, for example, Cl.

84-1-a)

84-1-b)

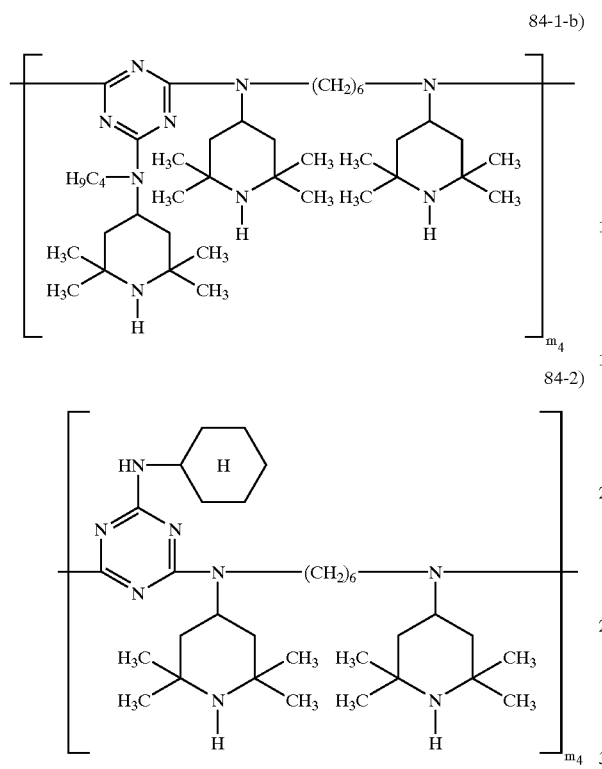

84-2)

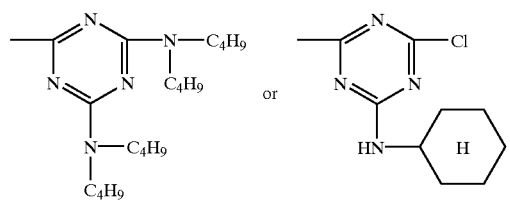

It may be convenient to replace the chlorine attached to the triazine by e.g. —OH or an amino group. Suitable amino groups are typically: pyrrolidin-1-yl, morpholino, —NH$_2$, —N(C$_1$–C$_8$alkyl)$_2$ and —NY'(C$_1$–C$_8$alkyl) wherein Y' is hydrogen or a group of the formula

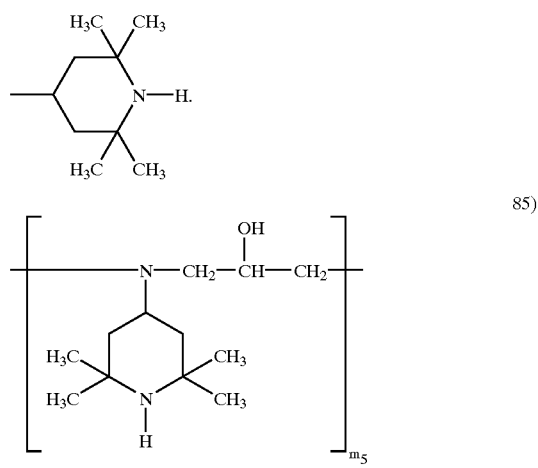

85)

In the compound 85, the end group bonded to the 2,2,6,6-tetramethylpiperidin-4-ylamino residue can be, for example, hydrogen and the end group bonded to the 2-hydroxypropylene residue can be, for example,

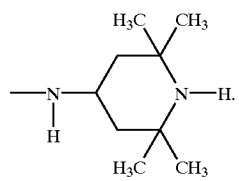

In the compounds 84-1-a, 84-1-b and 84-2, the end group bonded to the triazine residue can be, for example, chlorine or a group

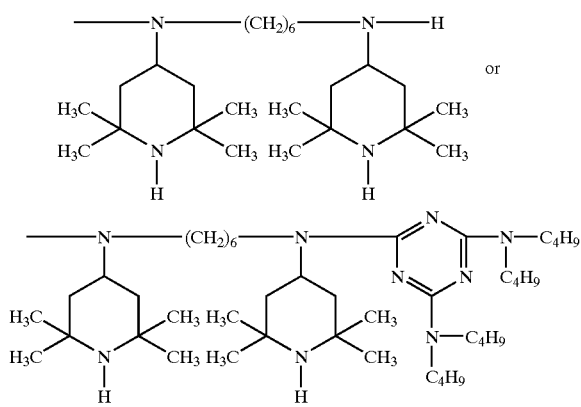

and the end group bonded to the diamino group can be, for example, hydrogen or a group

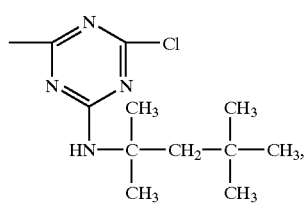

86)

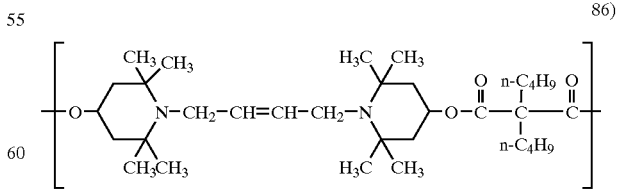

In the compound 86, the end group bonded to the —O— can be, for example, hydrogen or

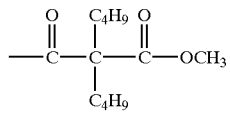

and the end group bonded to the diacyl residue can be, for example, —OCH₃ or Cl.

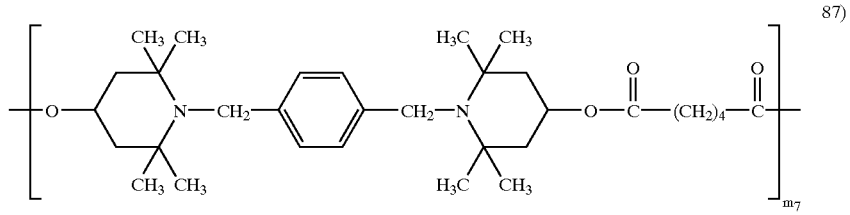

In the compound 87, the end group bonded to the —O— can be, for example, hydrogen or

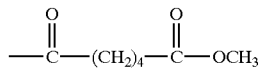

and the end group bonded to the diacyl radical can be, for example, —OCH₃ or Cl.

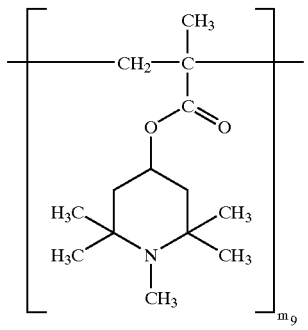

In the compound 89, the end group bonded to the —CH₂— can be, for example, hydrogen and the end group bonded to the ester residue can be, for example,

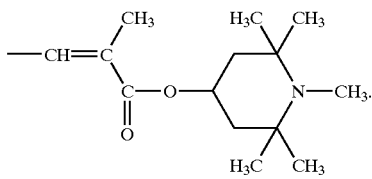

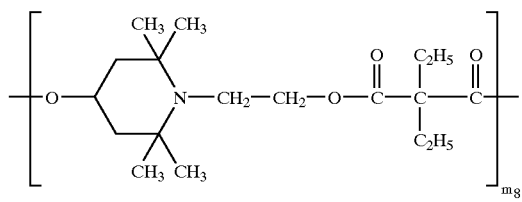

In the compound 88, the end group bonded to the —O— can be, for example, hydrogen or

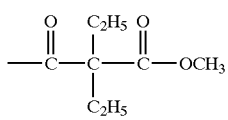

and the end group bonded to the diacyl radical can be, for example, —OCH₃ or Cl.

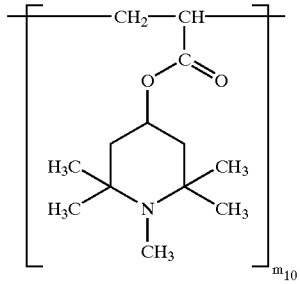

In the compound 90, the end group bonded to the —CH$_2$— can be, for example, hydrogen and the end group bonded to the ester residue can be, for example,

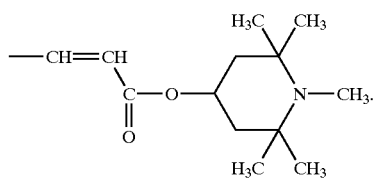

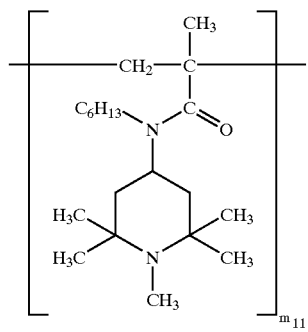

In the compound 91, the end group bonded to the —CH$_2$— can be, for example, hydrogen and the end group bonded to the amide residue can be, for example,

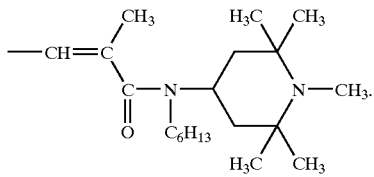

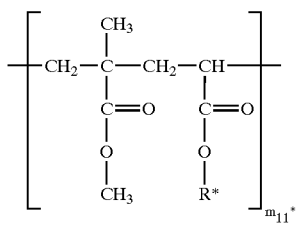

wherein $m_{11}^{\star}$ is as defined for $m_{11}$, the radicals R$^{\star}$ independently of one another are ethyl or 2,2,6,6-tetramethylpiperidin-4-yl, with the proviso that at least 50% of the radicals R$^{\star}$ are 2,2,6,6-tetramethylpiperidin-4-yl and the remaining radicals R$^{\star}$ are ethyl. In the compound 91-1), the terminal groups are for example hydrogen.

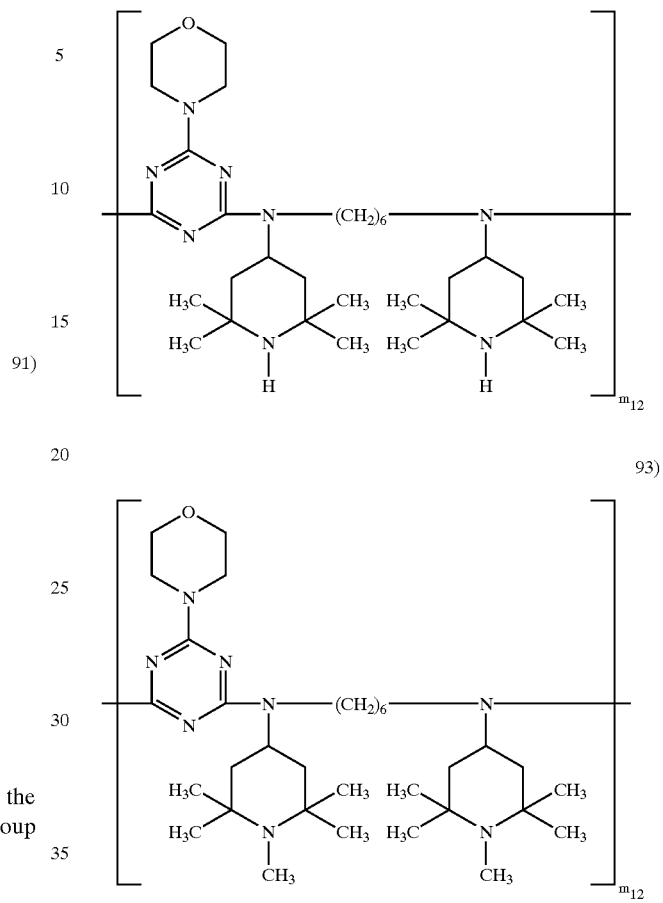

In the compounds 92 and 93, the end group bonded to the triazine residue can be, for example, chlorine or a group

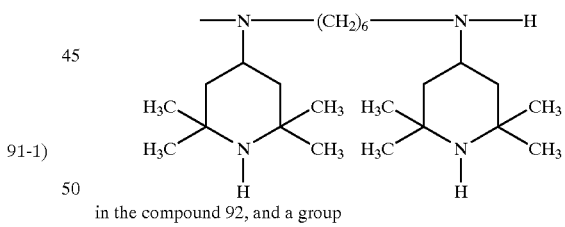

in the compound 92, and a group

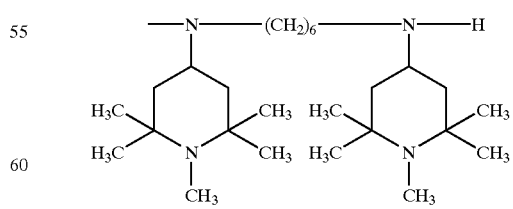

in the compound 93, and the end group bonded to the diamino residue can be, for example, hydrogen or a group

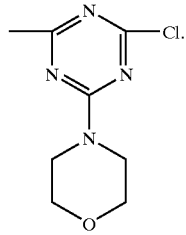

It may be convenient to replace the chlorine attached to the triazine by e.g. —OH or an amino group. Suitable amino groups are typically: pyrrolidin-1-yl, morpholino, —NH$_2$, —N(C$_1$–C$_8$alkyl)$_2$ and —NY'(C$_1$–C$_8$alkyl) wherein Y' is hydrogen or a group of the formula

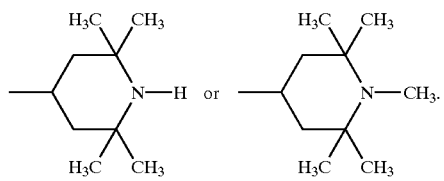

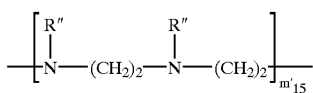

(94)

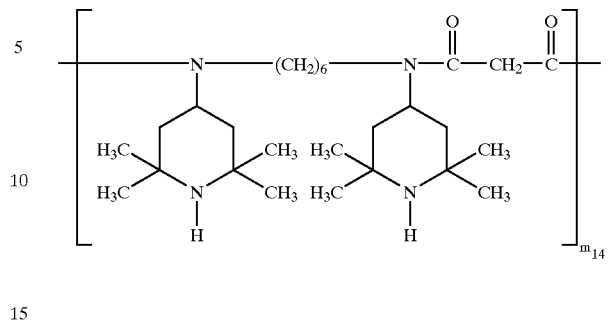

(95)

In the compound 95, the end group bonded to the diamino residue can be, for example, hydrogen and the end group bonded to the diacyl residue can be, for example, Cl.

(96)

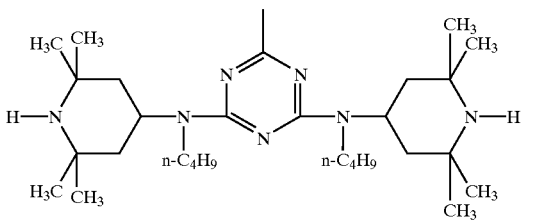

in which R" is a group of the formula (96-I)

or the chain branching

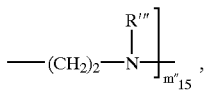

R''' is a group of the formula (96-1), and m'$_{15}$ and m''$_{15}$ are each a number from 0 to 200, preferably 0 to 100, in particular 0 to 50, with the proviso that m'$_{15}$+m''$_{15}$ is a number from 2 to 200, preferably 2 to 100, in particular 2 to 50. In the compound 96, the end group bonded to the diamino residue can be, for example, hydrogen and the end group bonded to the —CH$_2$CH$_2$— group can be, for example, halogen, in particular Cl or Br.

In the compound 94, the end group bonded to the diamino residue can be, for example, hydrogen and the end group bonded to the —CH$_2$CH$_2$— residue can be, for example,

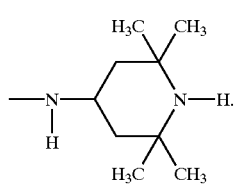

Further examples for polymeric compounds are:
1) A compound of the formula (97)

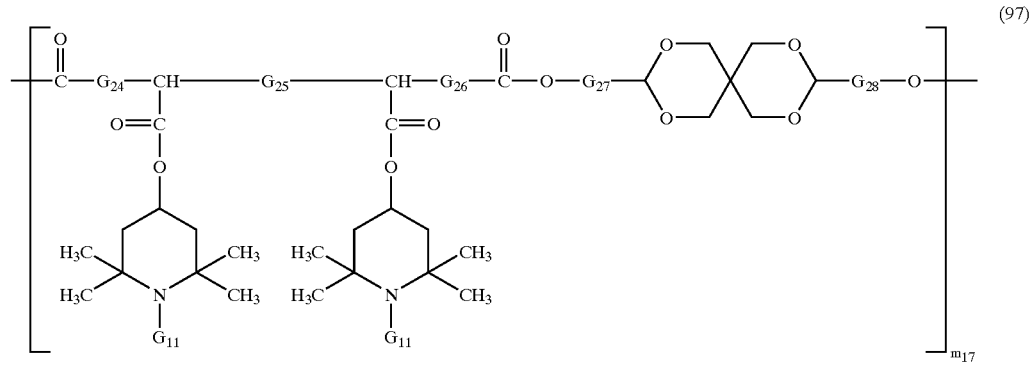

wherein $G_{24}$, $G_{25}$, $G_{26}$, $G_{27}$ and $G_{28}$, independently of one another, are a direct bond or $C_1$–$C_{10}$alkylene, $G_{11}$ is as defined under (a') and $m_{17}$ is a number from 1 to 50.

In the compound of the formula (97), the end group bonded to the >C=O group can be, for example,

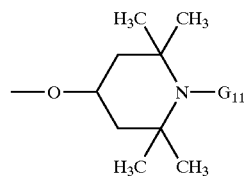

and the end group bonded to the oxygen can be, for example

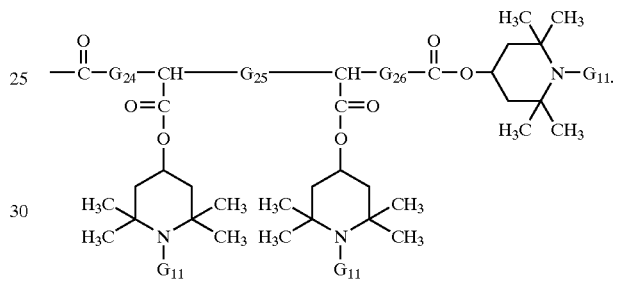

Preferred are the following two compounds:

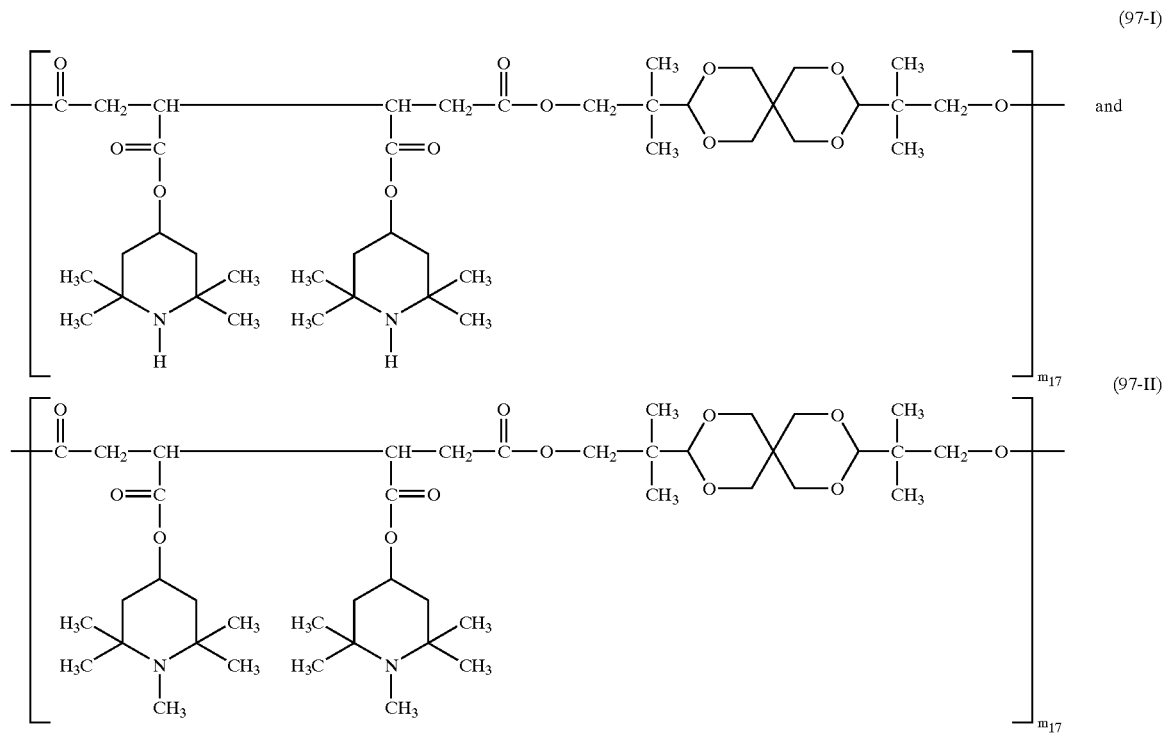

wherein $m_{17}$ is a number from 1 to 20.

2) A compound of the formula (98)

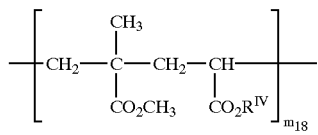

in which approximately one third of the radicals $R^{IV}$ are —$C_2H_5$ and the others are a group

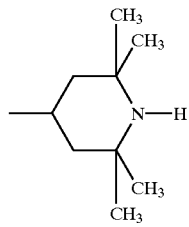

and $m_{18}$ is a number in the range from 2 to 200, preferably 2 to 100, in particular 2 to 50.

In the compound (98), the end group bonded to the —$CH_2$— residue can be, for example, hydrogen and the end group bonded to the —$CH(CO_2R^{IV})$— residue can be, for example, —CH=CH—$COOR^{IV}$.

3) A compound of the formula (99)

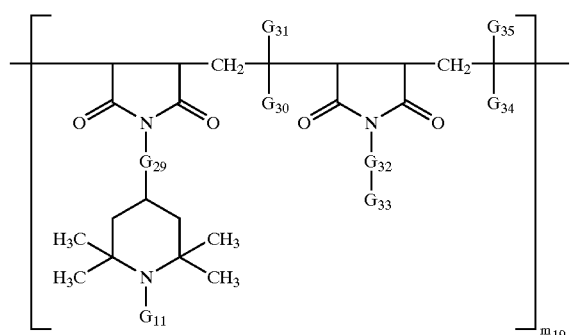

in which $G_{11}$ is as defined under (a'), $G_{29}$ and $G_{32}$, independently of one another, are a direct bond or a —$N(X_1)$—CO—$X_2$—CO—$N(X_3)$— group, where $X_1$, and $X_3$, independently of one another, are hydrogen, $C_1$–$C_8$alkyl, $C_5$–$C_{12}$cycloalkyl, phenyl, $C_7$–$C_9$phenylalkyl or a group of the formula (99-1)

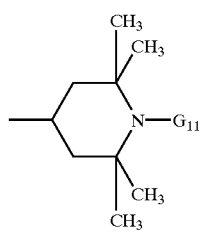

and $X_2$ is a direct bond or $C_1$–$C_4$alkylene, $G_{30}$, $G_{31}$, $G_{34}$ and $G_{35}$, independently of one another, are hydrogen, $C_1$–$C_{30}$alkyl, $C_5$–$C_{12}$cycloalkyl or phenyl, $G_{33}$ is hydrogen, $C_1$–$C_{30}$alkyl, $C_5$–$C_{12}$cycloalkyl, $C_7$–$C_9$phenylalkyl, phenyl or a group of the formula (99-1), and $m_{19}$ is a number from 1 to 50.

In the compounds of the formula (99), the end group bonded to the 2,5-dioxopyrrolidine ring can be, for example, hydrogen, and the end group bonded to the —$C(G_{34})$ ($G_{35}$)— radical can be, for example,

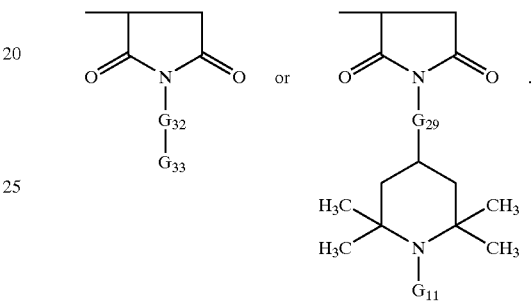

Examples of the compounds of the formula (99) are:

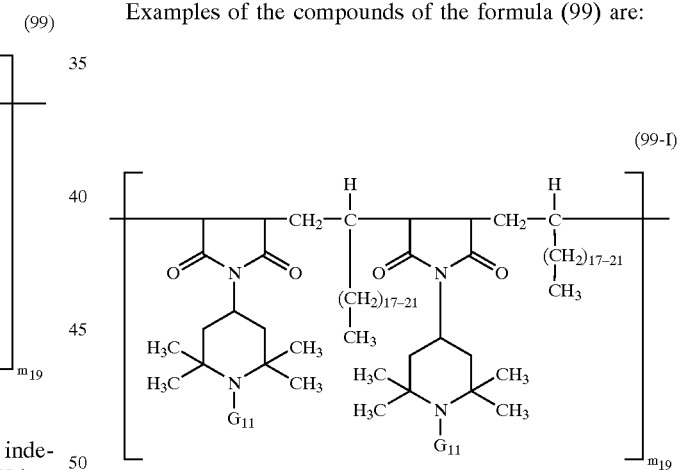

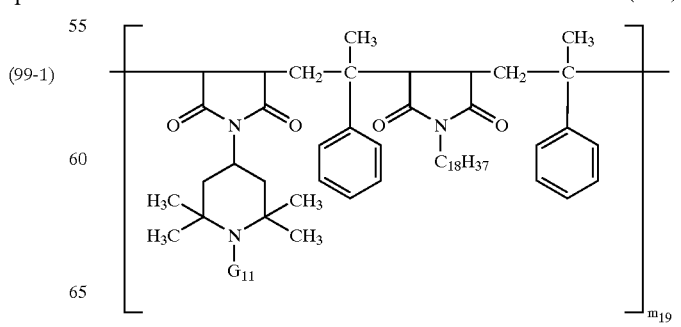

-continued (99-III)

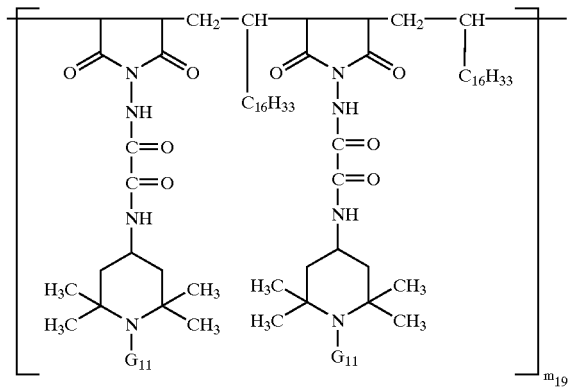

wherein $G_{11}$ is hydrogen or methyl, and $m_{19}$ is a number from 1 to 25.

4) A product obtainable by reacting an intermediate product, obtained by reaction of a polyamine of the formula (100a) with cyanuric chloride, with a compound of the formula (100b)

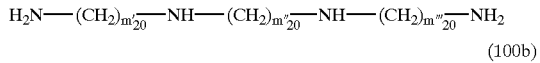

(100a)

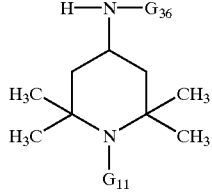

(100b)

in which $m'_{20}$, $m''_{20}$ and $m'''_{20}$, independently of one another, are a number from 2 to 12, $G_{36}$ is hydrogen, $C_1$–$C_{12}$alkyl, $C_5$–$C_{12}$cycloalkyl, phenyl or $C_7$–$C_9$phenylalkyl, and $G_{11}$ is as defined under (a'). A preferred product has the Chemical Abstracts-CAS No. 136 504-96-6 (Compound 100-A).

In general, the above reaction product can be represented for example by a compound of the formula 100-1, 100-2 or 100-3. It can also be in the form of a mixture of these three compounds.

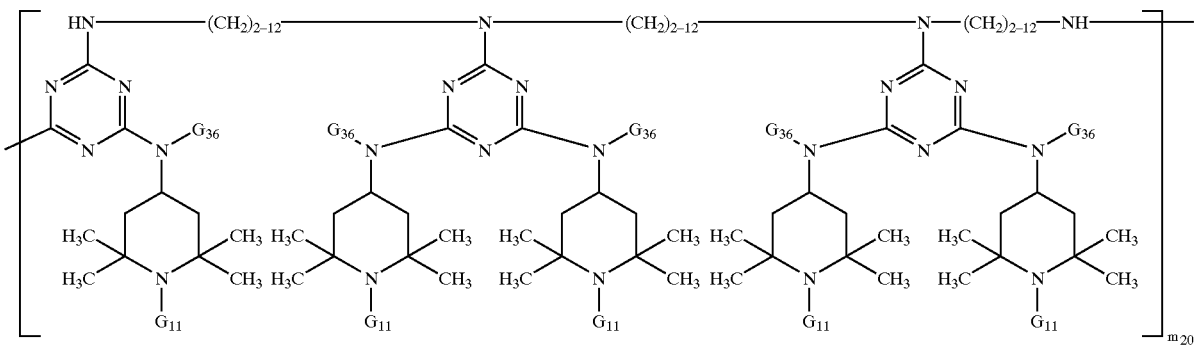

(100-1)

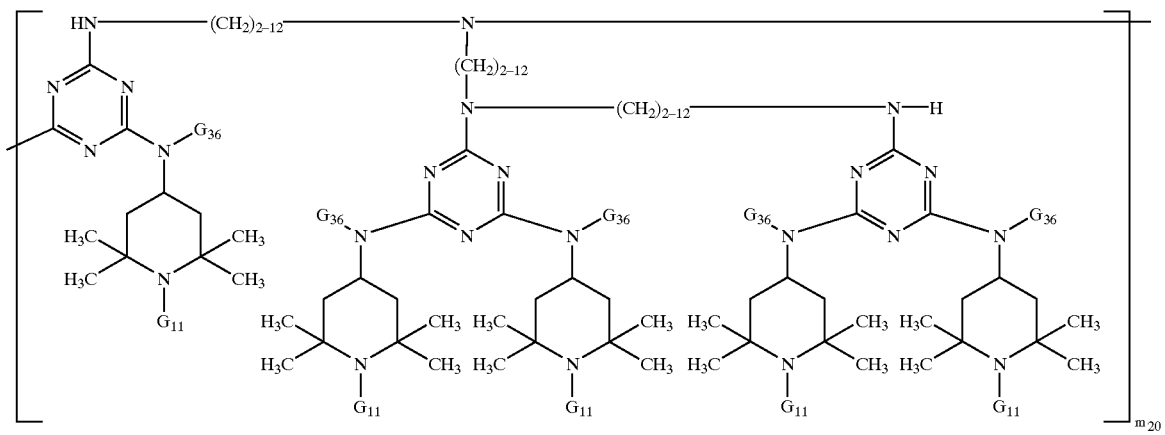

(100-2)

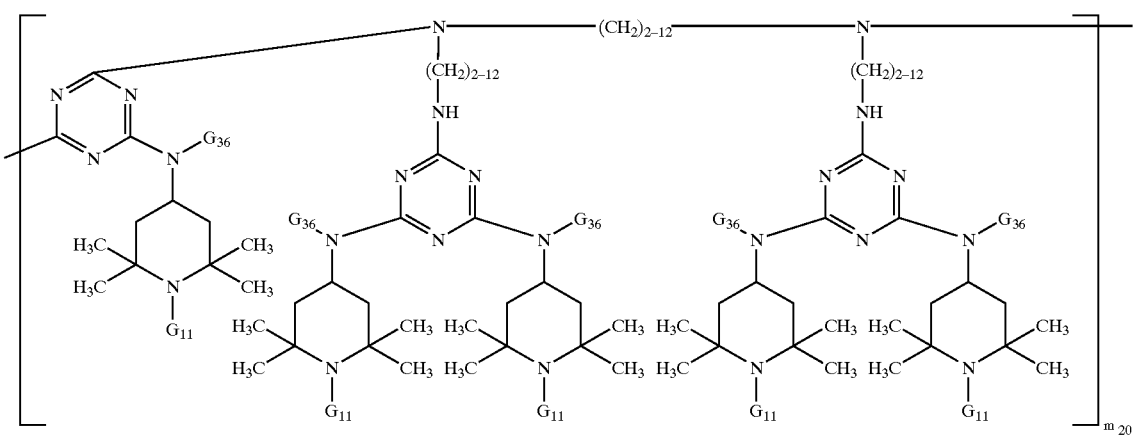
(100-3)
A preferred meaning of the formula (100-1) is
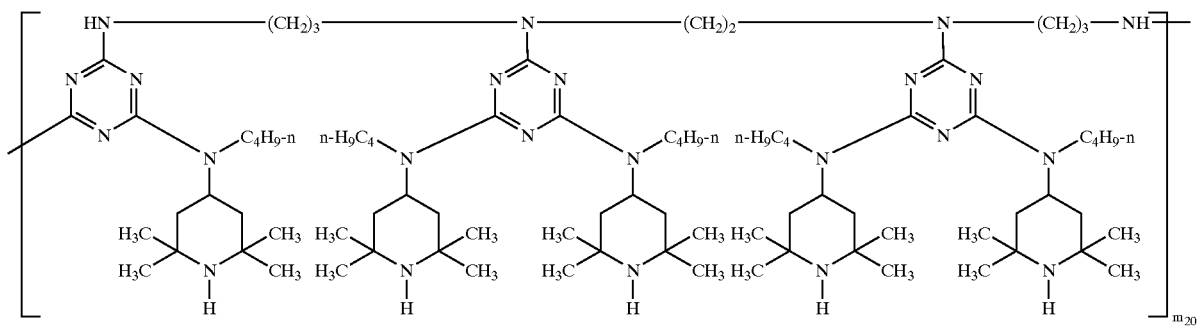
A preferred meaning of the formula (100-2) is
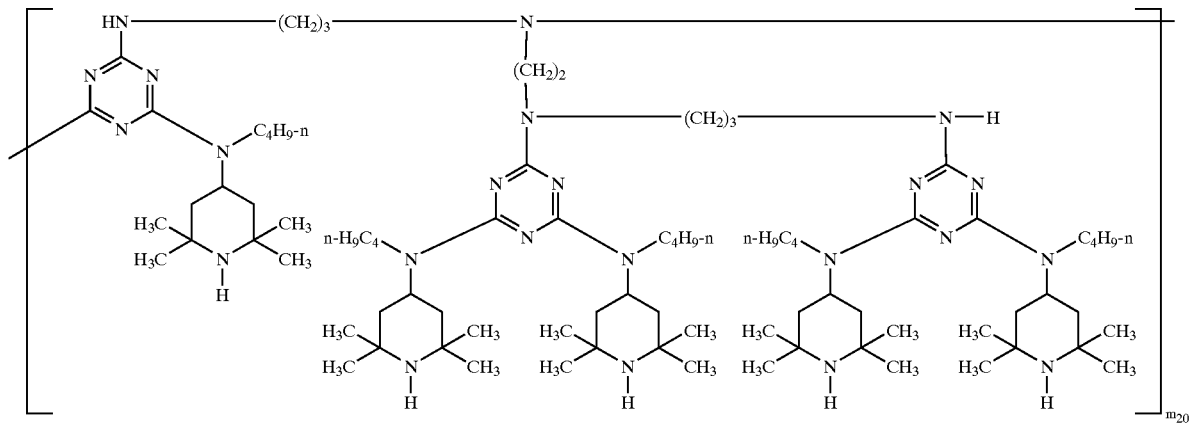

A preferred meaning of the formula (100-3) is

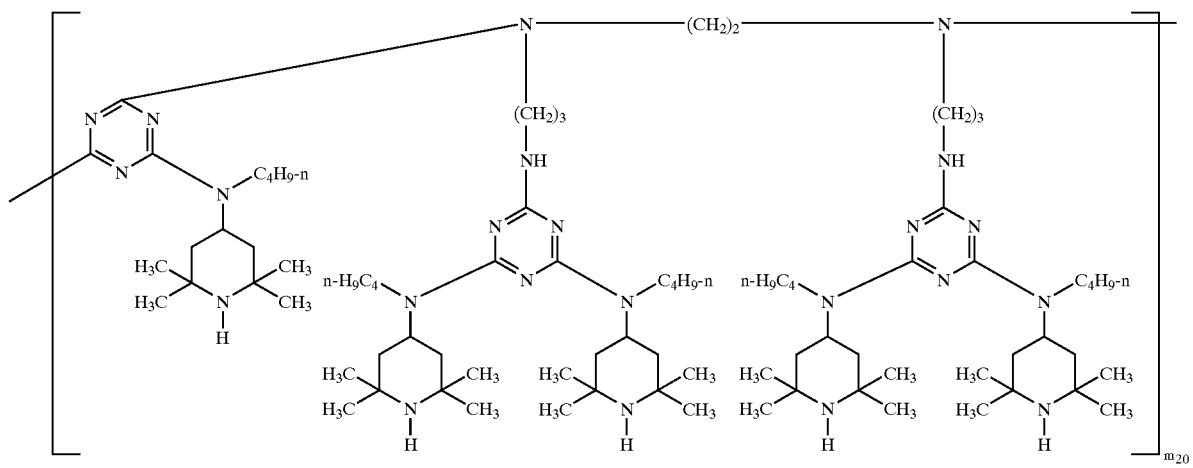

In the above formulae 100-1 to 100-3, $m_{20}$ is preferably 2 to 20, in particular 2 to 10.

5) A compound of the formula (101)

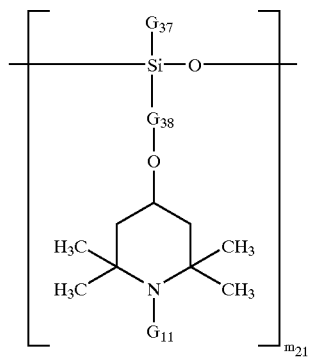

(101)

in which $G_{11}$ is as defined under (a'), $G_{37}$ is $C_1$–$C_{10}$alkyl, $C_5$–$C_{12}$cycloalkyl, $C_1$–$C_4$alkyl-substituted $C_5$–$C_{12}$cycloalkyl, phenyl or $C_1$–$C_{10}$alkyl-substituted phenyl, $G_{38}$ is $C_3$–$C_{10}$alkylene and $m_{21}$ is a number from 1 to 50.

In the compounds of the formula (101), the terminal group bonded to the silicon atom can be, for example, $(G_{37})_3$Si—O—, and the terminal group bonded to the oxygen can be, for example, —Si$(G_{37})_3$.

The compounds of the formula (101) can also be in the form of cyclic compounds if $m_{21}$ is a number from 3 to 10, i.e. the free valences shown in the structural formula then form a direct bond.

An example of a compound of the formula (101) is

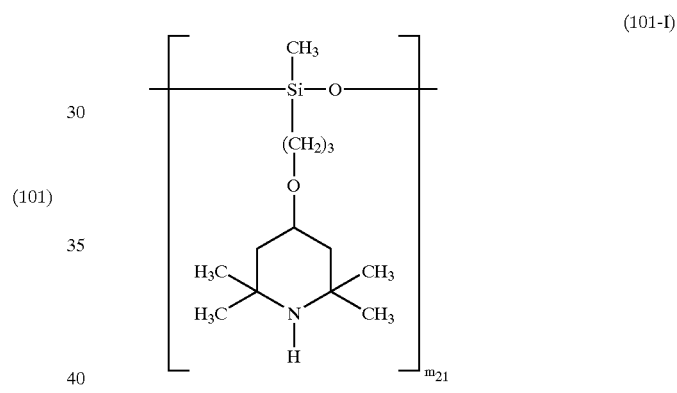

(101-I)

with $m_{21}$, being a number from 1 to 20, for example 2 to 20.

In the above shown oligomeric and polymeric compounds, examples of alkyl are methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethyl-hexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, eicosyl and docosyl; examples of cycloalkyl are cyclopentyl, cyclohexyl, cycloheptyl and cyclooctyl; an example of $C_7$–$C_9$phenylalkyl is benzyl; and examples of alkylene are ethylene, propylene, trimethylene, tetramethylene, pentamethylene, 2,2-dimethyltrimethylene, hexamethylene, trimethylhexamethylene, octamethylene and decamethylene.

(h') A compound of the formula (Ih)

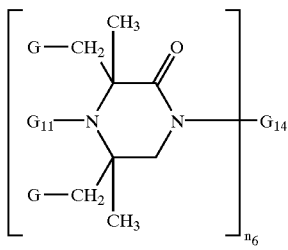

(Ih)

in which $n_6$ is the number 1 or 2, G and $G_{11}$ are as defined under (a'), and $G_{14}$ is as defined under (b'), but $G_{14}$ cannot be —CONH—Z and —CH$_2$—CH(OH)—CH$_2$—O—D—O—.

Examples of such compounds are the following:

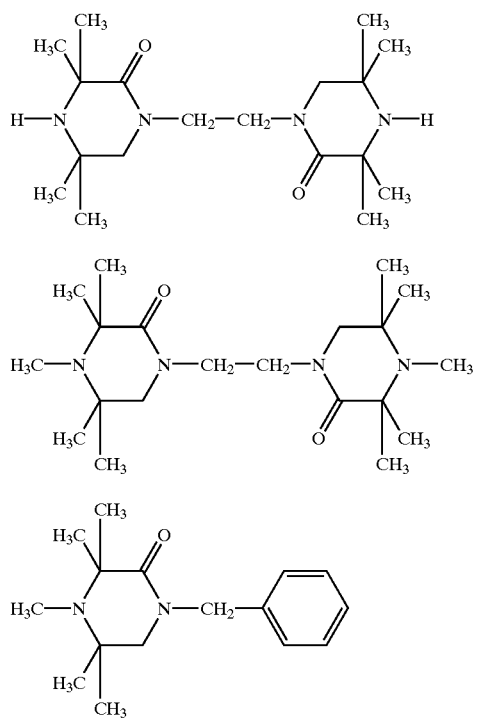

102)

103)

104)

(i') A compound of the formula (Ii)

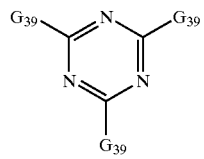

(Ii)

wherein the radicals $G_{39}$, independently of one another, are a group of the formula (Ii-1)

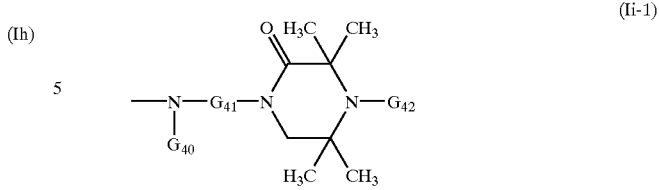

(Ii-1)

in which $G_{40}$ is $C_1$–$C_{12}$alkyl or $C_5$–$C_{12}$cycloalkyl, $G_{41}$ is $C_2$–$C_{12}$alkylene and $G_{42}$ is hydrogen, $C_1$–$C_8$alkyl, —O, —CH$_2$CN, $C_3$–$C_6$alkenyl, $C_7$–$C_9$phenylalkyl, $C_7$–$C_9$phenylalkyl which is substituted on the phenyl radical by $C_1$–$C_4$alkyl; or $C_1$–$C_8$acyl.

Alkyl is for example $C_1$–$C_4$alkyl, in particular methyl, ethyl, propyl or butyl.

Cycloalkyl is preferably cyclohexyl.

Alkylene is for example ethylene, propylene, trimethylene, tetramethylene, pentamethylene, 2,2-dimethyltrimethylene or hexamethylene.

Alkenyl is preferably allyl.

Phenylalkyl is preferably benzyl.

Acyl is preferably acetyl.

Examples of compounds from this class are the compounds of the following formulae:

105)

106)

The compound 5), 13), 14), 49-a-1), 49-a-2), 49-d), 63), 76), 84-1-a), 84-1-b), 84-2), 91-1), 92), 93), 97-I), 97-I), 99-1), 100-A), 105), 106) or 101-1) correspond to a preferred example of component B).

The component (C) of the stabilizer mixture according to this invention is anatase which is a specific crystalline form of TiO$_2$. Examples of commercially available anatase are:

®Bayertitan A (®Bayer),
®Bayertitan A-E (®Bayer),
®Bayertitan A-N-2 (®Bayer),
®Bayertitan A-Z (®Bayer),
®Bayertitan T (®Bayer),
®Kronos A (®Kronos),
®Kronos AD (®Kronos),
®Kronos APF (®Kronos),
®Kronos AV (®Kronos),
®Hombitan LOCR (®Sachtleben),
®Hombitan LOCR-K (®Sachtleben),
®Hombitan LW (®Sachtleben), ®Tiona AG (®SCM(GB)),
®Tiona WDB (®SCM(GB)),
®Titafrance AT 1 (®Thann),
®Titafrance AT 3 (®Thann),
®Tioxide A-HR (®Tioxide), and
®Tioxide A-PP 2 (®Tioxide), The component (B) of the present stabilizer mixture is preferably
di(2,2,6,6-tetramethylpiperidin-4-yl)sebacate,
di(1-octyloxy-2,2,6,6-tetramethylpiperidin-4-yl)sebacate,
di(1,2,2,6,6-pentamethylpiperidin-4-yl)sebacate,
8-acetyl-3-dodecyl-1,3,8-triaza-7,7,9,9-tetramethylspiro[4.5]decane-2,4-dione,
di(1,2,2,6,6-pentamethylpiperidin-4-yl) butyl(3,5-di-tert-butyl-4-hydroxybenzyl)malonate,

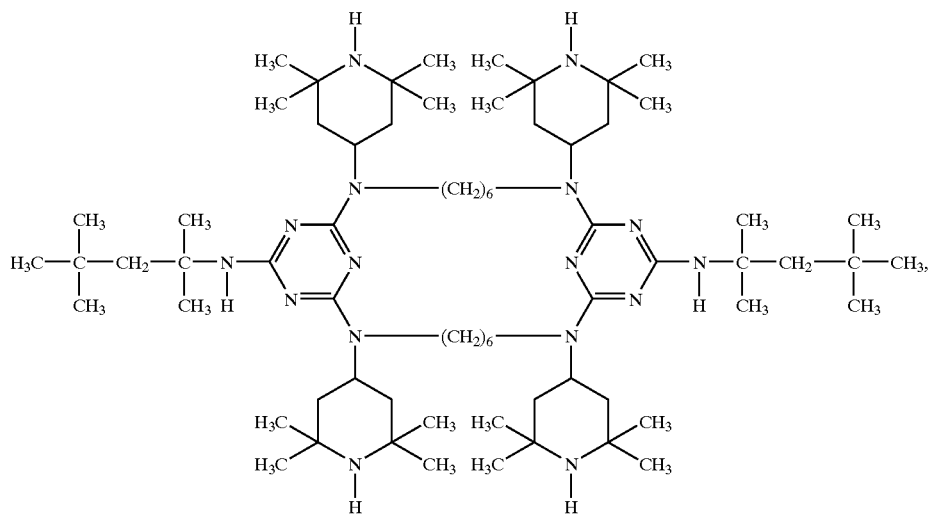

4-stearoyloxy-2,2,6,6-tetramethylpiperidine,
1-(2,2,6,6-tetramethylpiperidin-4-ylamino)-2-(2,2,6,6-tetramethylpiperidin-4-ylaminocarbonyl)ethane,

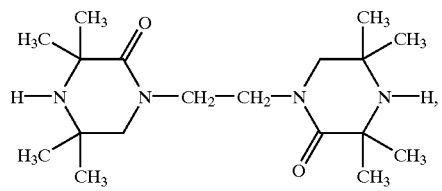

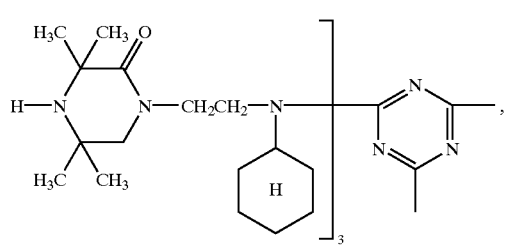

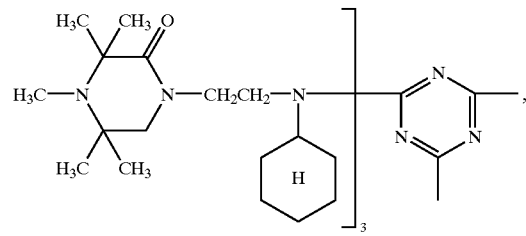

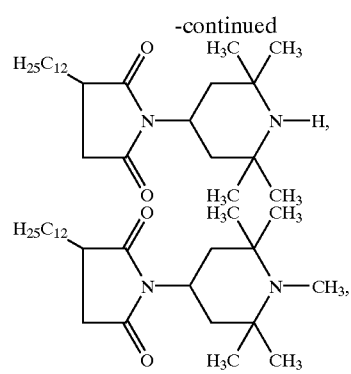

2,2,4,4-tetramethyl-7-oxa-3,20-diaza-21-oxodispiro[5.1.11.2]heneicosane, with $R_0$ being $C_{12}$–$C_{14}$alkyl, 1,2,3,4-tetrakis[1,2,2,6,6-pentamethylpiperidin-4-yloxycarbonyl]butane,
1,2,3,4-tetrakis[2,2,6,6-tetramethylpiperidin-4-yloxycarbonyl]butane,
bis[1,2,2,6,6-pentamethylpiperidin-4-yloxycarbonyl]-bis[tridecyloxycarbonyl]butane,
bis[2,2,6,6-tetramethylpiperidin-4-yloxycarbonyl]-bis[tridecyloxycarbonyl]butane,
2-(2,2,6,6-tetramethylpiperidin-4-ylamino)-2-(2,2,6,6-tetramethylpiperidin-4-ylaminocarbonyl)propane,

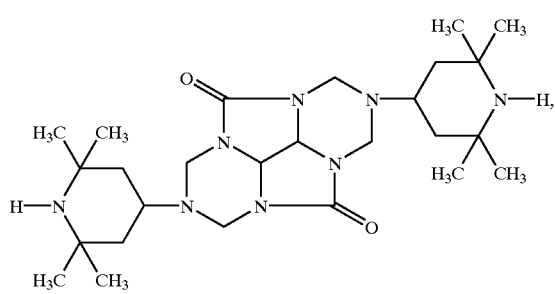

1,6-bis[N-(2,2,6,6-tetramethylpiperidin-4-yl)formylamino]hexane,

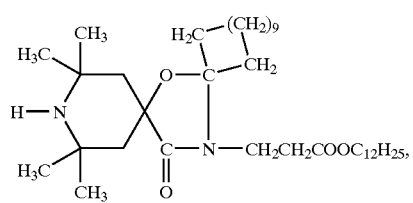

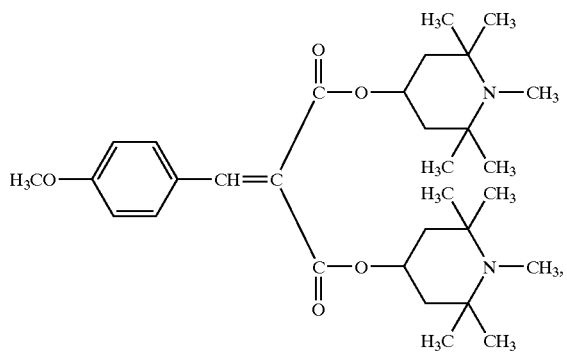

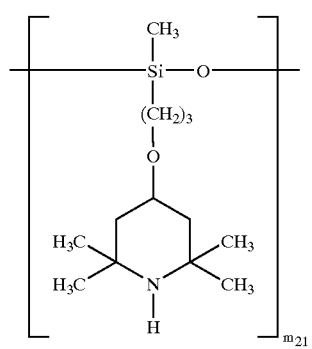

with $m_{21}$ being a number from 1 to 20,

-continued

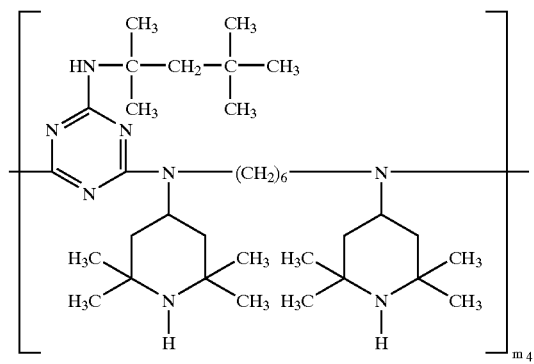

with $m_4$ being a number from 2 to 50,

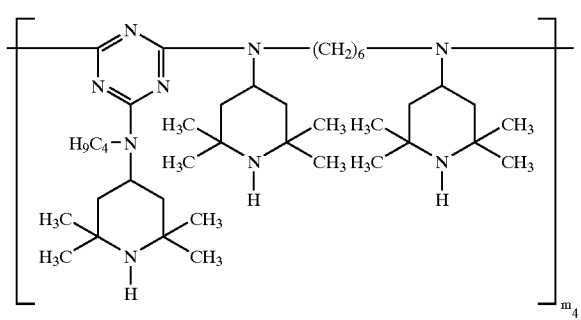

with $m_4$ being a number from 2 to 50,

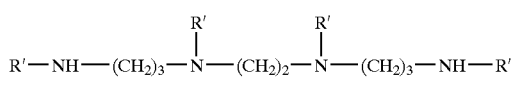

with R' being

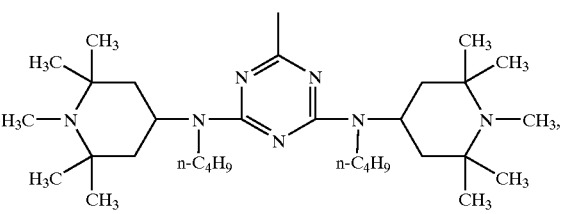

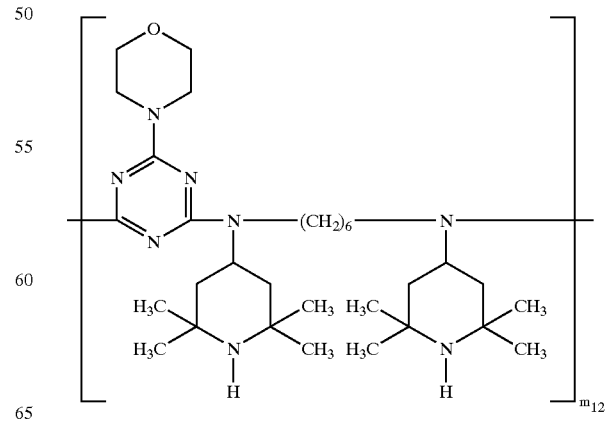

with $m_{12}$ being a number from 2 to 50,

-continued

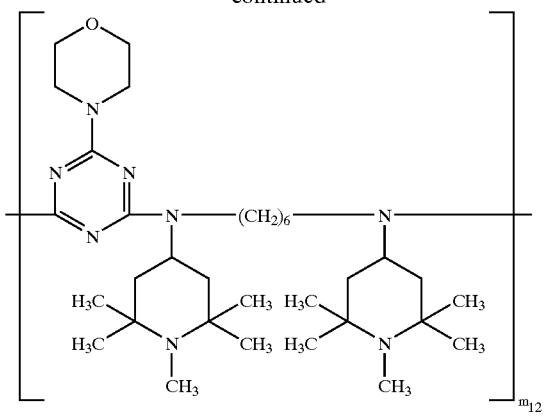

with $m_{12}$ being a number from 2 to 50,

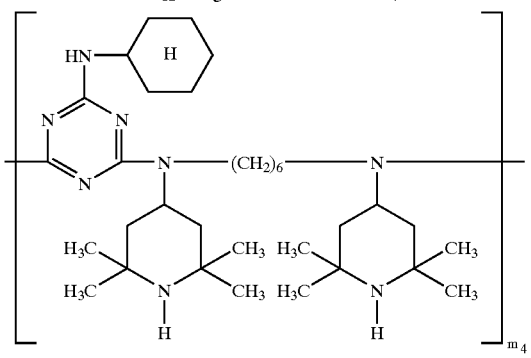

with $m_4$ being a number from 2 to 50,

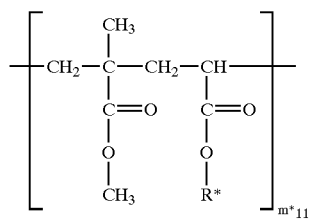

wherein $m_{11}^\star$ is a number from 2 to 50, the radicals $R^\star$ independently of one another are ethyl or 2,2,6,6-tetramethylpiperidin-4-yl, with the proviso that at least 50% of the radicals $R^\star$ are 2,2,6,6-tetramethylpiperidin-4-yl and the remaining radicals $R^\star$ are ethyl,

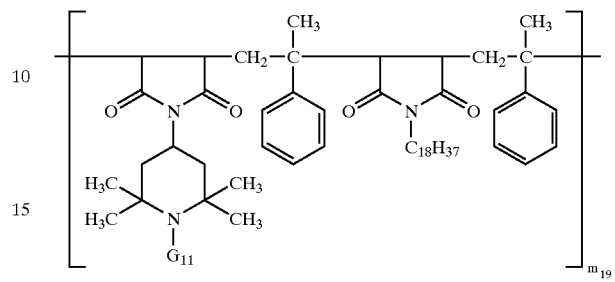

with $m_{19}$ being a number from 1 to 25 and $G_{11}$ being hydrogen or methyl,

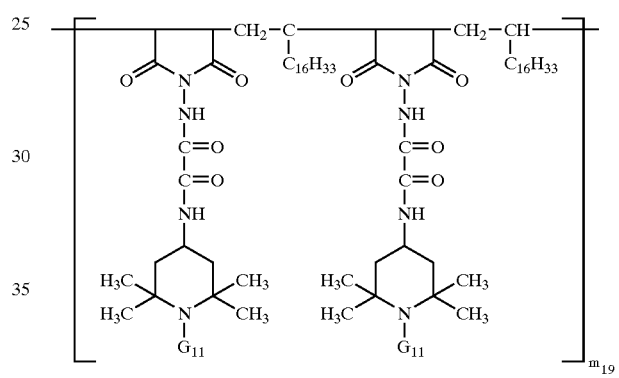

with $m_{19}$ being a number from 1 to 25 and $G_{11}$, being hydrogen or methyl,

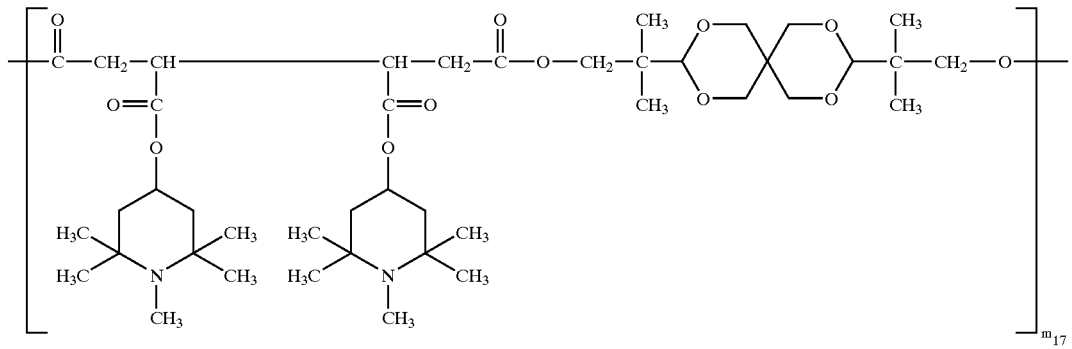

with $m_{17}$ being a number from 1 to 20,

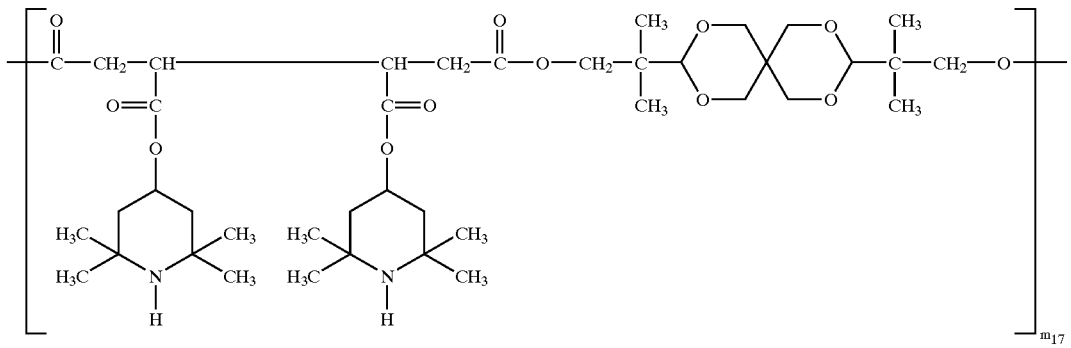

with $m_{17}$ being a number from 1 to 20,

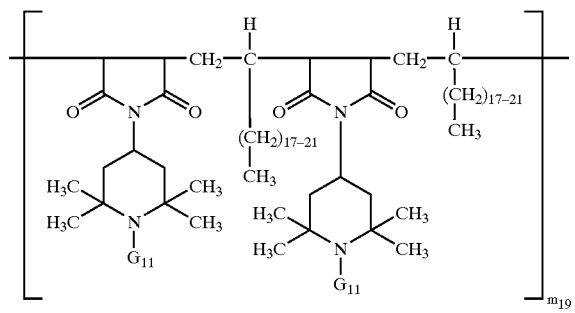

with $m_{19}$ being a number from 1 to 25 and $G_{11}$ being hydrogen or methyl, or a product obtainable by reacting an intermediate product, obtained by reaction of a polyamine of the formula (100a) with cyanuric chloride, with a compound of the formula (100b)

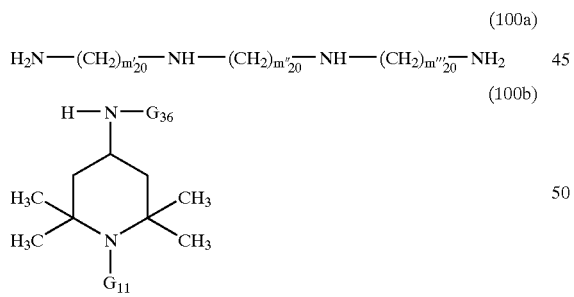

in which $m'_{20}$, $m''_{20}$ and $m'''_{20}$, independently of one another, are a number from 2 to 12, $G_{36}$ is hydrogen, $C_1$–$C_{12}$alkyl, $C_5$–$C_{12}$cycloalkyl, phenyl or $C_7$–$C_9$phenylalkyl, and $G_{11}$ is hydrogen or methyl.

Component (B) is in particular the commercially available product ®TINUVIN 770, ®TINUVIN 123, ®TINUVIN 765, TINUVIN 440, ®TINUVIN 144, ®CHIMASSORB 966, ®DASTIB 845, ®DIACETAM 5, ®GOODRITE UV 3034, ®GOODRITE UV 3150, ®GOODRITE UV 3159, ®CYASORB UV 3581, ®CYASORB UV 3604, ®HOSTAVIN N 20, ®HOSTAVIN N 24, ®MARK LA 52, ®MARK LA 57, ®MARK LA 62, ®MARK LA 67, ®SUMISORB TM 61, ®UVINUL 4049, ®UVINUL 4050H, ®SANDUVOR 3050, ®SANDUVOR PR-31, ®UVASIL 299 LM, ®UVASIL 2000 LM, ®CHIMASSORB 944, ®CHIMASSORB 2020, ®CHIMASSORB 119, ®CYASORB UV 3346, ®CYASORB UV 3529, ®DASTIB 1082, ®FERRO AM 806, ®LICHTSCHUTZSTOFF UV 31, ®LUCHEM HA-B18, ®MARK LA 63, ®MARK LA 68, ®UVINUL 5050H, ®UVASIL 299 HM, ®UVASIL 2000 HM or ®UVASORB HA 88.

According to a preferred embodiment the component (B) is di(2,2,6,6-tetramethylpiperidin-4-yl) sebacate, di(1,2,2,6,6-pentamethylpiperidin-4-yl) sebacate,

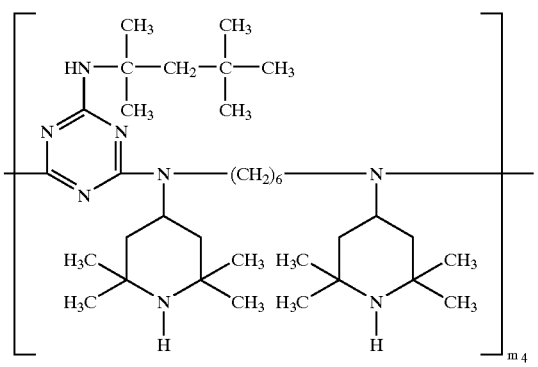

with $m_4$ being a number from 2 to 50,

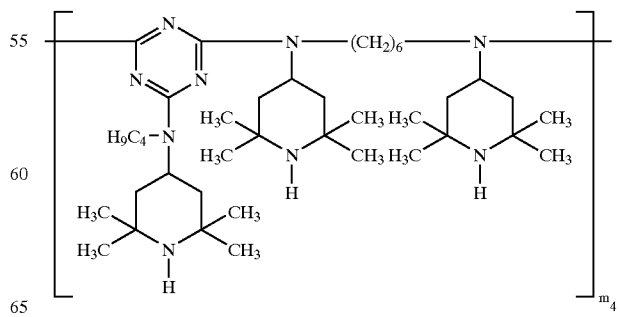

with $m_4$ being a number from 2 to 50, di(2,2,6,6-tetramethylpiperidin-4-yl) sebacate;

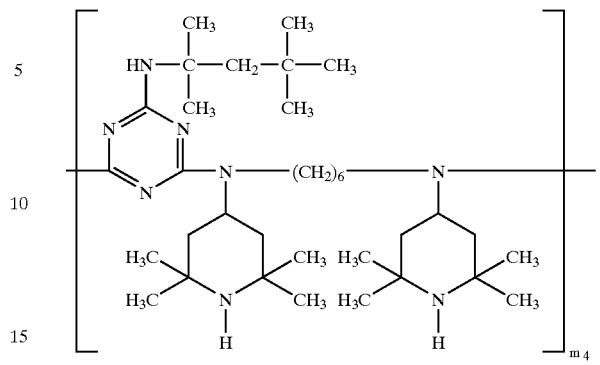

with m₄ being a number from 2 to 50;

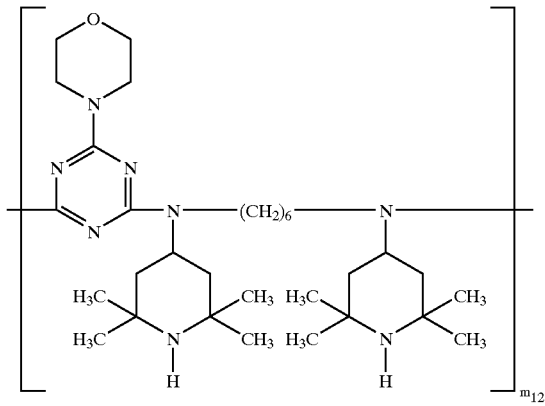

with m₁₂ being a number from 2 to 50, or

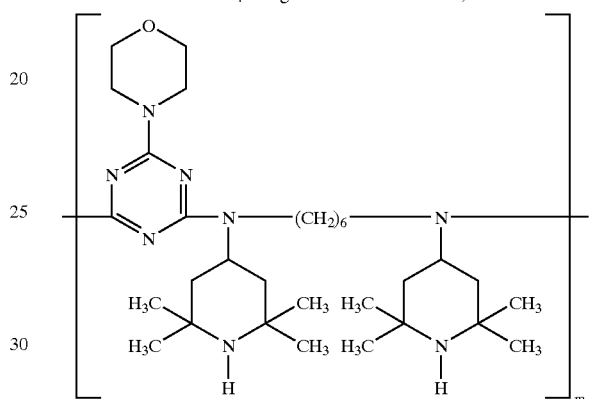

with m₁₂ being a number from 2 to 50;

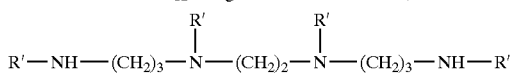

with R' being

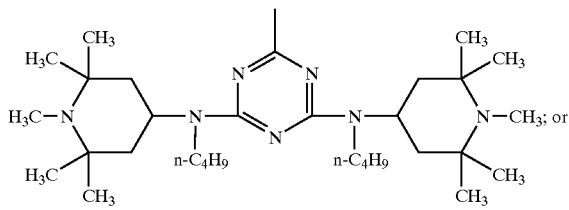

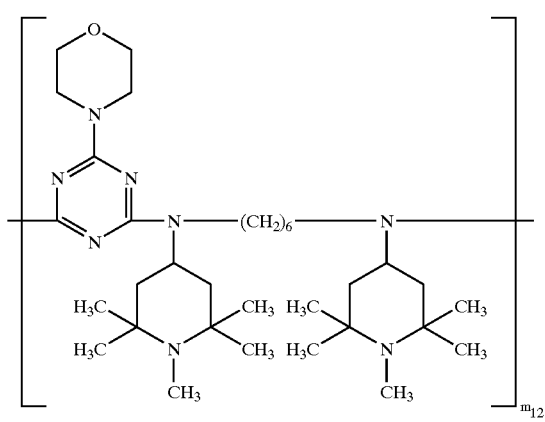

with m₁₂ being a number from 2 to 50.

A particularly preferred embodiment of this invention relates to a stabilizer mixture wherein the component (A) is

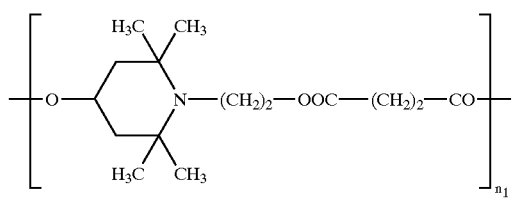

with $n_1$ being a number from 2 to 20, and the component (B) is a product obtainable by reacting an intermediate product, obtained by reaction of a polyamine of the formula (100a-1) with cyanuric chloride, with a compound of the formula (100b-1).

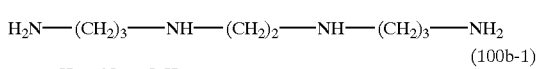
(100a-1)

(100b-1)

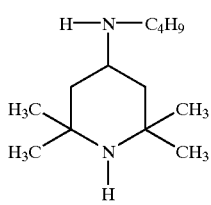

A further particularly preferred embodiment of this invention relates to a stabilizer mixture wherein the component (A) is

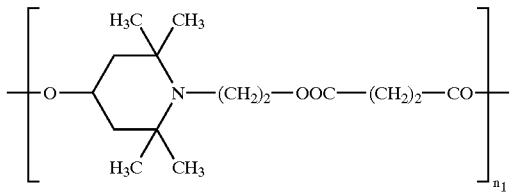

Examples of stabilizer mixtures according to the present invention are:
1. ®TINUVIN 622+®TINUVIN 770+anatase.
2. ®TINUVIN 622+®TINUVIN 123+anatase.
3. ®TINUVIN 622+®TINUVIN 765+anatase.
4. ®TINUVIN 622+®TINUVIN 440+anatase.
5. ®TINUVIN 622+®TINUVIN 144+anatase.
6. ®TINUVIN 622+®CHIMASSORB 966+anatase.
7. ®TINUVIN 622+®DASTIB 845+anatase.
8. ®TINUVIN 622+®DIACETAM 5+anatase.
9. ®TINUVIN 622+®GOODRITE UV 3034+anatase.
10. ®TINUVIN 622+®GOODRITE UV 3150+anatase.
11. ®TINUVIN 622+®GOODRITE UV 3159+anatase.
12. ®TINUVIN 622+®CYASORB UV 3581+anatase.
13. ®TINUVIN 622+®CYASORB UV 3604+anatase.
14. ®TINUVIN 622+®HOSTAVIN N 20+anatase.
15. ®TINUVIN 622+®HOSTAVIN N 24+anatase.
16. ®TINUVIN 622+®MARK LA 52+anatase.
17. ®TINUVIN 622+®MARK LA 57+anatase.
18. ®TINUVIN 622+®MARK LA 62+anatase.
19. ®TINUVIN 622+®MARK LA 67+anatase.
20. ®TINUVIN 622+®SUMISORB TM 61+anatase.
21. ®TINUVIN 622+®UVINUL 4049+anatase.
22. ®TINUVIN 622+®UVINUL 4050H+anatase.
23. ®TINUVIN 622+®SANDUVOR 3050+anatase.
24. ®TINUVIN 622+®SANDUVOR PR-31+anatase.
25. ®TINUVIN 622+®UVASIL 299 LM+anatase.
26. ®TINUVIN 622+®UVASIL 2000 LM+anatase.
27. ®TINUVIN 622+®CHIMASSORB 944+anatase.
28. ®TINUVIN 622+®CHIMASSORB 2020+anatase.
29. ®TINUVIN 622+®CHIMASSORB 119+anatase.
30. ®TINUVIN 622+®CYASORB UV 3346+anatase.
31. ®TINUVIN 622+®CYASORB UV 3529+anatase.
32. ®TINUVIN 622+®DASTIB 1082+anatase.
33. ®TINUVIN 622+®FERRO AM 806+anatase.
34. ®TINUVIN 622+®LICHTSCHUTZSTOFF UV 31+anatase.
35. ®TINUVIN 622+®LUCHEM HA-B18+anatase.
36. ®TINUVIN 622+®MARK LA 63+anatase.
37. ®TINUVIN 622+®MARK LA 68+anatase.
38. ®TINUVIN 622+®UVINUL 5050H+anatase.
39. ®TINUVIN 622+®UVASIL 299 HM+anatase.
40. ®TINUVIN 622+®UVASIL 2000 HM+anatase.
41. ®TINUVIN 622+®UVASORB HA 88+anatase.
42. ®HOSTAVIN N 30+®TINUVIN 770+anatase.
43. ®HOSTAVIN N 30+®TINUVIN 123+anatase.
44. ®HOSTAVIN N 30+®TINUVIN 765+anatase.
45. ®HOSTAVIN N 30+®TINUVIN 440+anatase.
46. ®HOSTAVIN N 30+®TINUVIN 144+anatase.
47. ®HOSTAVIN N 30+®CHIMASSORB 966+anatase.
48. ®HOSTAVIN N 30+®DASTIB 845+anatase.
49. ®HOSTAVIN N 30+®DIACETAM 5+anatase.
50. ®HOSTAVIN N 30+®GOODRITE UV 3034+anatase.
51. ®HOSTAVIN N 30+®GOODRITE UV 3150+anatase.
52. ®HOSTAVIN N 30+®GOODRITE UV 3159+anatase.
53. ®HOSTAVIN N 30+®CYASORB UV 3581+anatase.
54. ®HOSTAVIN N 30+®CYASORB UV 3604+anatase.
55. ®HOSTAVIN N 30+®HOSTAVIN N 20+anatase.
56. ®HOSTAVIN N 30+®HOSTAVIN N 24+anatase.
57. ®HOSTAVIN N 30+®MARK LA 52+anatase.
58. ®HOSTAVIN N 30+®MARK LA 57+anatase.
59. ®HOSTAVIN N 30+®MARK LA 62+anatase.
60. ®HOSTAVIN N 30+®MARK LA 67+anatase.
61. ®HOSTAVIN N 30+®SUMISORB TM 61+anatase.
62. ®HOSTAVIN N 30+®UVINUL 4049+anatase.
63. ®HOSTAVIN N 30+®UVINUL 4050H+anatase.
64. ®HOSTAVIN N 30+®SANDUVOR 3050+anatase.
65. ®HOSTAVIN N 30+®SANDUVOR PR-31+anatase.
66. ®HOSTAVIN N 30+®UVASIL 299 LM+anatase.
67. ®HOSTAVIN N 30+®UVASIL 2000 LM+anatase.
68. ®HOSTAVIN N 30+®CHIMASSORB 944+anatase.
69. ®HOSTAVIN N 30+®CHIMASSORB 2020+anatase.
70. ®HOSTAVIN N 30+®CHIMASSORB 119+anatase.
71. ®HOSTAVIN N 30+®CYASORB UV 3346+anatase.
72. ®HOSTAVIN N 30+®CYASORB UV 3529+anatase.
73. ®HOSTAVIN N 30+®DASTIB 1082+anatase.
74. ®HOSTAVIN N 30+®FERRO AM 806+anatase.
75. ®HOSTAVIN N 30+®LICHTSCHUTZSTOFF UV 31+anatase.
76. ®HOSTAVIN N 30+®LUCHEM HA-B18+anatase.
77. ®HOSTAVIN N 30+®MARK LA 63+anatase.
78. ®HOSTAVIN N 30+®MARK LA 68+anatase.
79. ®HOSTAVIN N 30+®UVINUL 5050H+anatase.
80. ®HOSTAVIN N 30+®UVASIL 299 HM+anatase.
81. ®HOSTAVIN N 30+®UVASIL 2000 HM+anatase.
82. ®HOSTAVIN N 30+®UVASORB HA 88+anatase.

The above stabilizer mixtures 1, 27, 29, 30 and 82 are particularly preferred.

The above stabilizer mixture 42 is particularly useful for stabilizing high density polyethylene.

The stabilizer mixture according to this invention is suitable for stabilizing organic materials against degradation induced by light, heat or oxidation. Examples of such organic materials are the following:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE), or polyvinyl cyclohexane.

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly($\alpha$-methylstyrene).

6. Copolymers of styrene or $\alpha$-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

7. Graft copolymers of styrene or $\alpha$-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from $\alpha,\beta$-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/ butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimids, polyesterimids, polyhydantoins and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, isocyanates, isocyanurates, polyisocyanates or epoxy resins.

26. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

30. Aqueous emulsions of natural or synthetic rubber, e.g. natural latex or latices of carboxylated styrene/butadiene copolymers.

This invention therefore additionally relates to a composition comprising an organic material subject to degradation induced by light, heat or oxidation and the stabilizer mixture described herein above.

A further embodiment of the present invention is a method for stabilizing an organic material against degradation induced by light, heat or oxidation, which comprises incorporating into the organic material the stabilizer mixture described herein above.

The organic material is preferably a synthetic polymer, in particular from one of the above groups. Polyolefins are preferred and polyethylene, polypropylene, a polyethylene copolymer and a polypropylene copolymer are particularly preferred.

The stabilizer mixture according to the present invention is also particularly useful for stabilizing polyamides, for example those listed above under item 16.

The components (A), (B) and (C) may be added to the organic material to be stabilized either individually or mixed with one another.

Each of the components (A) and (B) may be present in the organic material in an amount of preferably 0.01 to 5%, in particular 0.01 to 1% or 0.05 to 1%, relative to the weight of the organic material.

The component (C) may be present in the organic material in an amount of preferably 0.01 to 10%, in particular 0.05 to 1%, for example 0.1 to 1%, relative to the weight of the organic material.

The weight ratio of the components (A):(B) is preferably 5:1 to 1:20, in particular 5:1 to 1:10, for example 2:1 to 1:2.

The weight ratio of the components (A):(C) is preferably 10:1 to 1:10, in particular 5:1 to 1:5, for example 3:1 to 1:3 or 2:1 to 1:2.

The above components can be incorporated into the organic material to be stabilized by known methods, for example before or during shaping or by applying the dissolved or dispersed compounds to the organic material, if necessary with subsequent evaporation of the solvent. The components can be added to the organic material in the form of a powder, granules or a masterbatch, which contains these components in, for example, a concentration of from 2.5 to 25% by weight.

If desired, the components (A), (B) and (C) can be blended with each other before incorporation in the organic material. They can be added to a polymer before or during the polymerization or before the crosslinking.

The materials stabilized according to this invention can be used in a wide variety of forms, for example as films, fibres, tapes, moulding compositions, profiles or as binders for paints, adhesives or putties.

The stabilized material may additionally also contain various conventional additives, for example:

1. Antioxidants 1.1. Alkylated monophenols, for example 2,6-di-tert-butyl-4-methylphenol, 2-tert-butyl-4,6-di-methylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl) phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis(2,6-dimethyl-4-hydroxyphenyl)disulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis-(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy-2-methylphenyl)pentane.

1.7. O—, N— and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, didodecymercaptoethyl-2,2-bis-(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine Compounds, for example 2,4-bis (octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris-(3,5-di-tert-butyl-4-hydroxyphenoxy)-1,2,3-triazine, 1,3,5-tris-(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris-(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis-(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β-(3.5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3.5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3.5-di-tert-butyl-4-hydroxyphenyl) propionic acid e.g. N,N'-bis(3,5-di-tert-butyl-4-hydroxyphenylpropionyl)hexamethylenediamide, N,N'-bis (3,5-di-tert-butyl-4-hydroxyphenylpropionyl)trimethylenediamide, N,N'-bis(3,5-di-tert-butyl-4-hydroxyphenylpropionyl)-hydrazide, N,N'-bis[2-(3-[3,5-di-tert-butyl-4-hydroxyphenyl]propionyloxy)ethyl]oxamide (Naugard® XL-1 supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenlenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino)-propane, (o-tolyl)biguamide, bis[4-(1',3'-dimethylbutyl)phenyl]amine, tert-octylated N-phenyl-1-naphthylamine, a mixture of mono- and dialkylated tert-butyl/tert-octyidiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- und dialkylated tert-butyldiphenylamines, 2,3-dihydro-3,3-dimethyl-4H-1,4-benzothiazine, phenothiazine, a mixture of mono- und dialkylated tert-butyl/tert-octylphenothiazines, a mixture of mono- und dialkylated tert-octyl-phenothiazines, N-allylphenothiazin, N,N,N',N'-tetraphenyl-1,4-diaminobut-2-ene, N,N-bis(2,2,6,6-tetramethylpiperid-4-yl-hexamethylenediamine, bis(2,2,6,6-tetramethylpiperid-4-yl) sebacate, 2,2,6,6-tetramethylpiperidin-4-one, 2,2,6,6-tetramethylpiperidin-4-ol.

2. UV Absorbers and Light Stabilisers 2.1. 2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-(α,β-dimethylbenzyl)-2'-hydroxyphenyl)benzotriazole, 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl)phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO—CH$_2$CH$_2$—]$_2$ where R=3'-tert-butyl-4'-hydroxy-5'-2H-benzotriazol-2-ylphenyl, 2-[2'-hydroxy-3'-(α,α-dimethylbenzyl)-5'-(1,1,3,3-tetramethylbutyl)-phenyl]-benzotriazole; 2-[2'-hydroxy-3'-(1,1,3,3-tetramethylbutyl)-5'-(α,α-dimethylbenzyl)-phenyl]benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutyl-phenyl salicylate, phenyl salicylate, octylphenyl salicylate, dibenzoyl resorcinol, bis (4-tert-butylbenzoyl) resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxy-cinnamate, butyl α-cyano-β-methyl-p-methoxy-cinnamate, methyl α-carbomethoxy-p-methoxycinnamate and N—(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.7. 2-(2-Hydroxyphenyl)-1.3.5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine, 2-[4-(dodecyloxy/tridecyloxy-2-hydroxypropoxy)-2-hydroxy-phenyl]-4,6-bis(2,4-dimethylphenyl)-1,3,5-triazine, 2-[2-hydroxy-4-(2-hydroxy-3-dodecyloxy-propoxy)phenyl]-4,6-bis(2,4-dimethyl-phenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxy-propoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl) oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butyl-phenyl) 4,4'-biphenylene diphosphonite, 6-isooctyloxy-2,4,8,10-tetra-tert-butyl-12H-dibenz-[d,g]-1,3,2-dioxaphosphocin, bis(2, 4-di-tert-butyl-6-methylphenyl) methyl phosphite, bis(2,4-di-tert-butyl-6-methylphenyl) ethyl phosphite, 6-fluoro-2,4, 8,10-tetra-tert-butyl-12-methyl-di-benz[d,g]-1,3,2-dioxaphosphocin, 2,2',2"-nitrilo[triethyltris(3,3',5,5'-tetra-tert-butyl-1,1'-biphenyl-2,2'-diyl)phosphite], 2-ethylhexyl (3,3',5,5'-tetra-tert-butyl-1,1'-biphenyl-2,2'-diyl)phosphite, 5-butyl-5-ethyl-2-(2,4,6-tri-tert-butylphenoxy)-1,3,2-dioxaphosphirane.

Especially preferred are the following phosphites:

Tris(2,4-di-tert-butylphenyl) phosphite (Irgafos® 168, Ciba-Geigy), tris(nonylphenyl) phosphite,

(A)

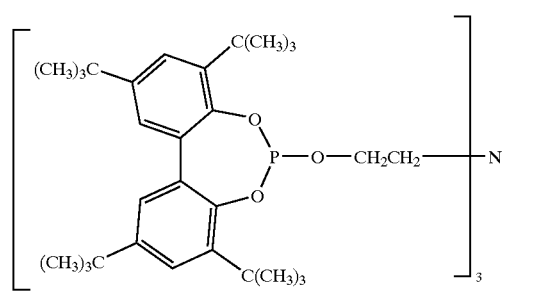
(B)

(C)

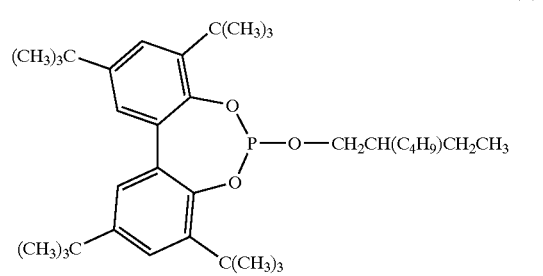

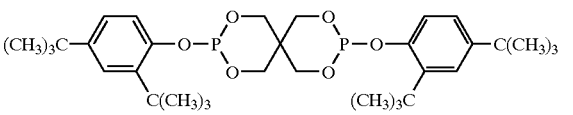
(D)

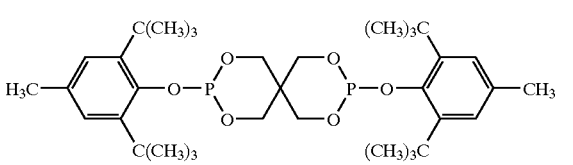
(E)

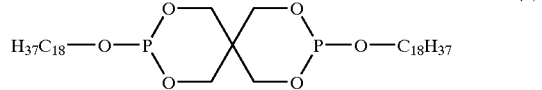
(F)

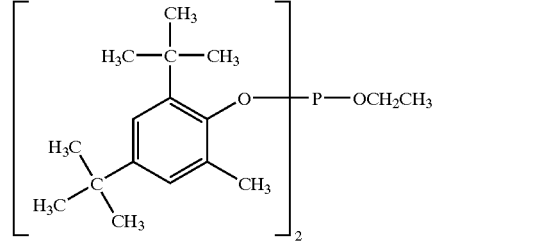
(G)

5. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example, N-benzyl-alpha-phenyl-nitrone, N-ethyl-alpha-methyl-nitrone, N-octyl-alpha-heptyl-nitrone, N-lauryl-alpha-undecyl-nitrone, N-tetradecyl-alpha-tridcyl-nitrone, N-hexadecyl-alpha-pentadecyl-nitrone, N-octadecyl-alpha-heptadecyl-nitrone, N-hexadecyl-alpha-heptadecyl-nitrone, N-ocatadecyl-alpha-pentadecyl-nitrone, N-heptadecyl-alpha-hepta-decyl-nitrone, N-octadecyl-alpha-hexadecyl-nitrone, nitrone derived from N,N-dialkylhydroxylamine derived from hydrogenated tallow amine.

7. Thiosynergists, for example, dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(p-dodecylmercapto)propionate.

9. Polyamide stabilisers, for example, copper salts in combination with iodides and/or phosphorus compounds and salts of divalent manganese.

10. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or zinc pyrocatecholate.

11. Nucleating agents, for example, inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers (ionomers). Especially preferred are 1,3:2,4-bis(3',4'-dimethylbenzylidene)sorbitol, 1,3:2,4-di(paramethyldibenzylidene)sorbitol, und 1,3:2,4-di(benzylidene)sorbitol.

12. Fillers and reinforcing agents, for example, calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

13. Other additives, for example, plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. No. 4,325,863; U.S. Pat. No. 4,338, 244; U.S. Pat. No. 5,175,312; U.S. Pat. No. 5,216,052; U.S. Pat. No. 5,252,643; DE-A-4316611; DE-A-4316622; DE-A-4316876; EP-A-0589839 or EP-A-0591102 or 3-[4-(2-acetoxyethoxy)phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one, 3-(3,4-dimethylphenyl)-5,7-di-tert-butyl-benzofuran-2-one, 3-(2,3-dimethylphenyl)-5,7-di-tert-butyl-benzofuran-2-one.

The weight ratio of the total amount of components (A), (B) and (C) to the total amount of the conventional additives can be, for example, 100:1 to 1:100 or 10:1 to 1:10.

The examples below illustrate the invention in greater detail. All percentages and parts are by weight, unless stated otherwise.

Stabilizers Used in the Following Examples 1 to 4:

Stablizer-(A-I-1):

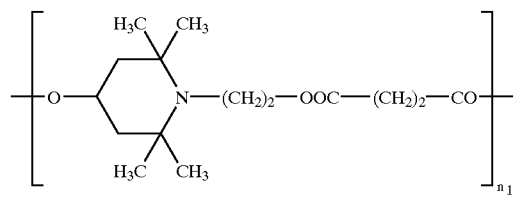

The mean value of $n_1$ is 5.1.

Stabilizer (A-II-1):
Mixture of the compounds (A-II-a) and (A-II-b) in a weight ratio of 4:1

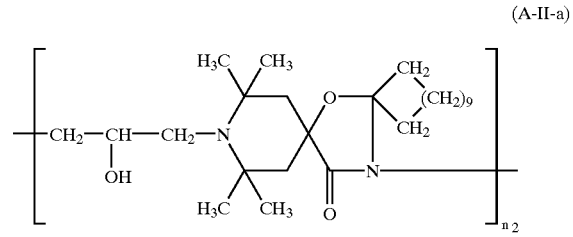

(A-II-a)

(A-II-b)

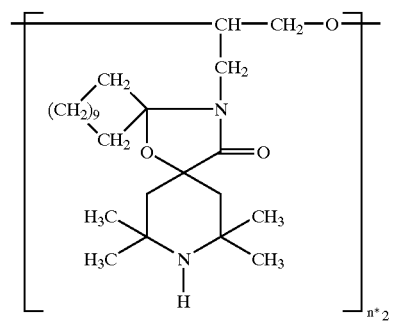

wherein the mean value of $n_2$ is 3.9 and the mean value of $n_2^*$ is 4.2.

Stabilizer (B-5-1):

Stabilizer (B-13):

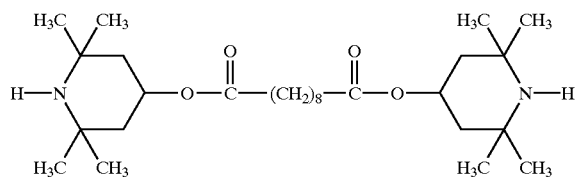

Stabilizer (B-14):

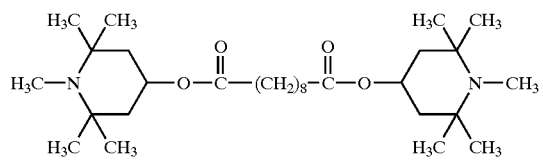

Stabilizer (B-49-d):
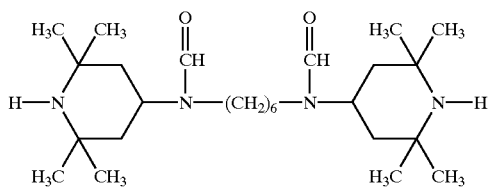
Stabilizer (B-63):
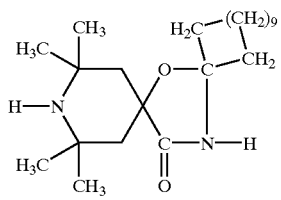
Stabilizer (B-76):
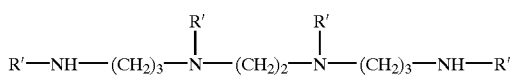
where R' is
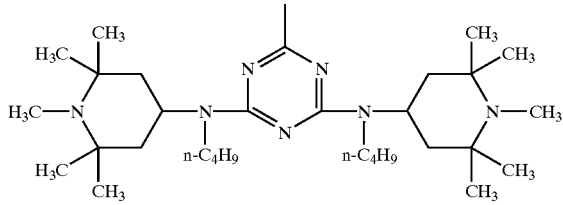
Stabilizer (B-84-1-a):
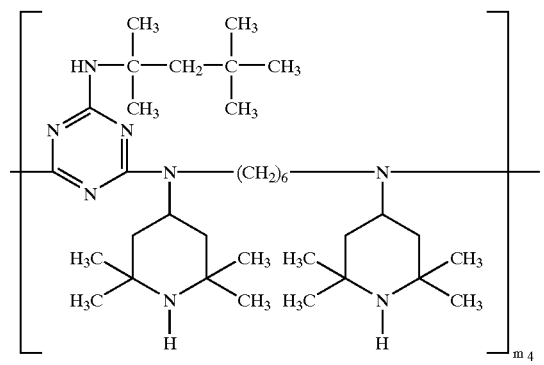
The mean value of $m_4$ is 4.5.
Stabilizer (B-92):
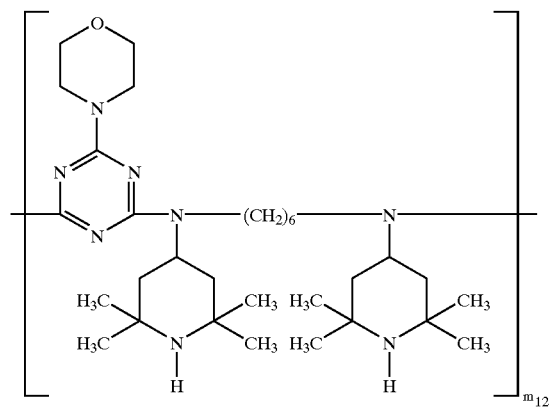
The mean value of $m_{12}$ is 3.5.
Stabilizer (B-97-I):
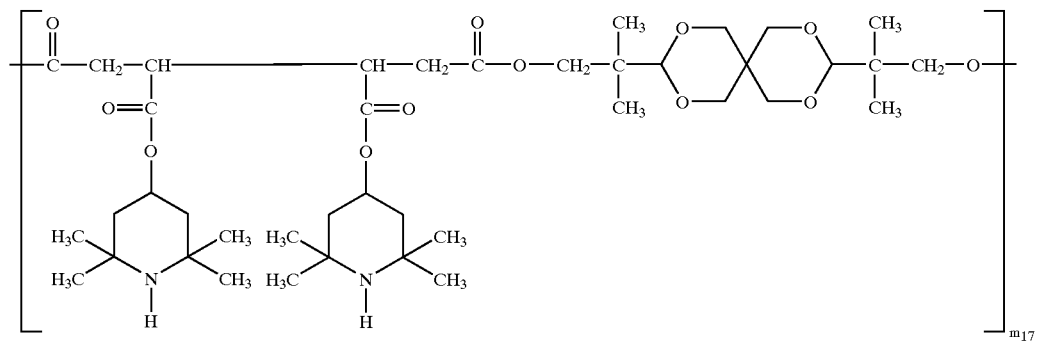
The mean value of $m_{17}$ is 2.5.

-continued
Stabilizer (B-97-II):
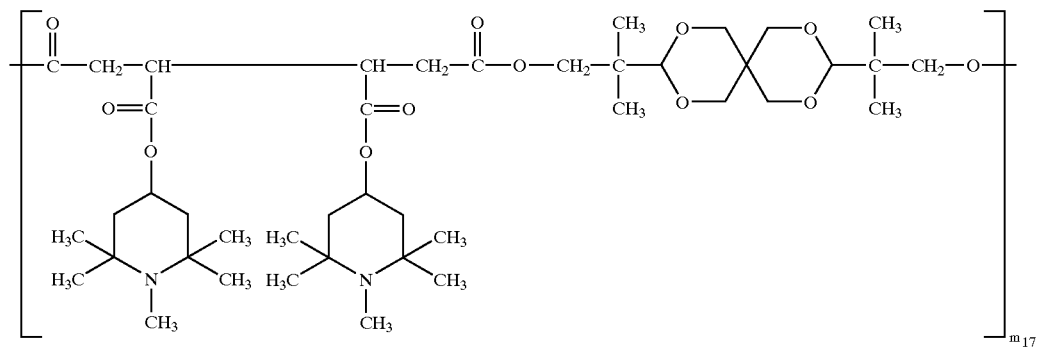
The mean value of $m_{17}$ is 2.5.
Stabilizer (B-99-I-1):
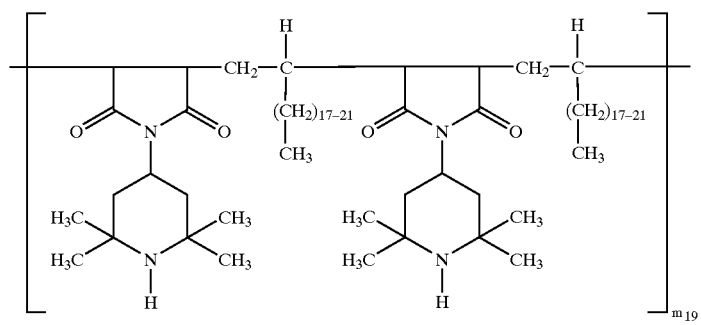
The mean value of $m_{19}$ is 3.2.
Stabilizer (B-100-A):
A product obtainable by reacting an intermediate product, obtained by reaction of a polyamine of the formula (100a-1) with cyanuric chloride, with a compound of the formula (100b-1).
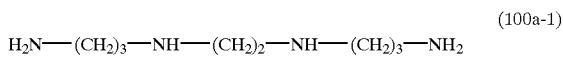  (100a-1)
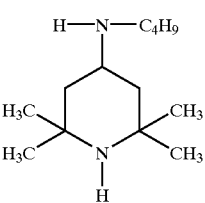  (100b-1)
Stabilizer (B-101-I):
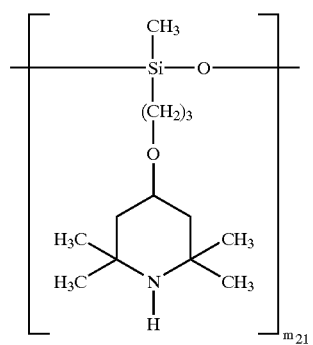
The mean value of $m_{21}$ is 5.8.
Stabilizer (B-105):
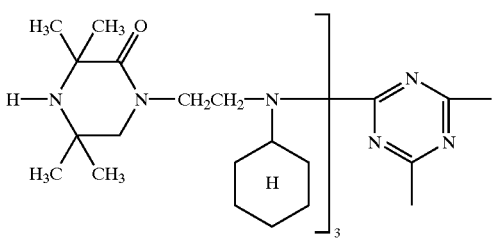

EXAMPLE 1

Light Stabilization of Polypropylene Homopolymer Films 100 parts of unstabilized polypropylene powder (melt flow index: 3.2 g/10 min at 230° C. and 2160 g) are homogenized at 200° C. for 10 min in a Brabender plastograph with 0.05 parts of pentaerythrityl-tetrakis{3-(3,5-di-tert-butyl-4-hydroxyphenyl)propionate}, 0.05 parts of tris{2,4-di-tert-butylphenyl} phosphite, 0.1 parts of Ca stearate and the stabilizer mixture indicated in Tables 1a and 1b. The material thus obtained is compression molded in a laboratory press between two aluminum foils for 6 min at 260° C. to a 0.5 mm thick film which is cooled immediately to room temperature in a water-cooled press. Samples of 60 mm×25 mm are cut out of these 0.5 mm films and are exposed in a WEATHER-OMETER Ci 65 (black panel temperature 63±2° C., without water-spraying).

Periodically, these samples are removed from the exposure apparatus and their carbonyl content is measured with an infrared spectrophotometer. The exposure time corresponding to formation of a carbonyl absorbance of 0.1 is a measure for the efficiency of the stabilizer mixture. The values obtained are summarized in Tables 1a and 1b.

TABLE 1a

| Stabilizer mixture | Time in hours until 0.1 carbonyl absorbance |
|---|---|
| 0.1% of (A-I-1) + 0.1% of (B-84-1-a) + 0.25% of anatase | 3140 |

TABLE 1b

| Stabilizer mixture | Time in hours until 0.1 carbonyl absorbance |
|---|---|
| 0.1% of (A-I-1) + 0.1% of (B-13) + 0.25% of anatase | 4775 |
| 0.1% of (A-II-1) + 0.1% (B-13) + 0.25% of anatase | 4455 |
| 0.1% of (A-I-1) + 0.1% of (B-14) + 0.25% of anatase | 4365 |
| 0.1% of (A-II-1) + 0.1% of (B-14) + 0.25% of anatase | 4860 |
| 0.1% of (A-I-1) + 0.1% of (B-5-1) + 0.25% of anatase | 3380 |
| 0.1% of (A-II-1) + 0.1% of (B-5-1) + 0.25% of anatase | 3650 |
| 0.1% of (A-I-1) + 0.1% of (B-63) + 0.25% of anatase | 2830 |
| 0.1% of (A-I-1) + 0.1% of (B-49-d) + 0.25% of anatase | 3250 |
| 0.1% of (A-I-1) + 0.1% of (B-105) + 0.25% of anatase | 3005 |
| 0.1% of (A-II-1) + 0.1% of (B-105) + 0.25% of anatase | 2505 |
| 0.1% of (A-I-1) + 0.1% of (B-84-1-a) + 0.25% of anatase | 3505 |
| 0.1% of (A-I-1) + 0.1% of (B-76) + 0.25% of anatase | 3155 |
| 0.1% of (A-I-1) + 0.1% of (B-92) + 0.25% of anatase | 3090 |
| 0.1% of (A-I-1) + 0.1% of (B-100-A) + 0.25% of anatase | 3350 |
| 0.1% of (A-I-1) + 0.1% of (B-101-I) + 0.25% of anatase | 4100 |
| 0.1% of (A-I-1) + 0.1% of (B-97-II) + 0.25% of anatase | 2435 |
| 0.1% of (A-I-1) + 0.1% of (B-97-I) + 0.25% of anatase | 2635 |

EXAMPLE 2

Light Stabilization of Polypropylene Homopolymer Films 100 parts of unstabilized polypropylene powder (melt flow index: 3.8 g/l 0 min at 230° C. and 2160 g) are homogenized at 200° C. for 10 min in a Brabender plastograph with 0.05 parts of pentaerythrityl-tetrakis{3-(3,5-di-tert-butyl-4-hydroxyphenyl)propionate},0.05 parts of tris{2, 4-di-tert-butylphenyl} phosphite, 0.1 parts of Ca stearate and the stabilizer mixture indicated in Table 2. The material thus obtained is compression molded in a laboratory press between two aluminum foils for 6 min at 260° C. to a 0.5 mm thick film which is cooled immediately to room temperature in a water-cooled press. Samples of 60 mm×25 mm are cut out of these 0.5 mm films and are exposed in a WEATHER-OMETER Ci 65 (black panel temperature 63±2° C., without water-spraying).

Periodically, these samples are removed from the exposure apparatus and their carbonyl content is measured with an infrared spectrophotometer. The exposure time corresponding to formation of a carbonyl absorbance of 0.1 is a measure for the efficiency of the stabilizer mixture. The values obtained are summarized in Table 2.

TABLE 2

| Stabilizer mixture | Time in hours until 0.1 carbonyl absorbance |
|---|---|
| 0.1% of (A-I-1) + 0.1% of (B-13) + 0.25% of anatase | 5980 |

EXAMPLE 3

Light Stabilization of Polypropylene Copolymer Films 100 parts of unstabilized polypropylene powder (melt flow index: 3.8 g/l 0 min at 230° C. and 2160 g) are homogenized at 200° C. for 10 min in a Brabender plastograph with 0.05 parts of pentaerythrityl-tetrakis{3-(3,5-di-tert-butyl-4-hydroxyphenyl)propionate}, 0.10 parts of tris{2,4-di-tert-butylphenyl} phosphite, 0.1 parts of Ca stearate and the stabilizer mixture indicated in Table 3. The material thus obtained is compression molded in a laboratory press between two aluminum foils for 6 min at 260° C. to a 0.5 mm thick film which is cooled immediately to room temperature in a water-cooled press. Samples of 60 mm×25 mm are cut out of these 0.5 mm films and are exposed in a WEATHER-OMETER Ci 65 (black panel temperature 63±2° C., without water-spraying).

Periodically, these samples are removed from the exposure apparatus and their carbonyl content is measured with an infrared spectrophotometer. The exposure time corresponding to formation of a carbonyl absorbance of 0.1 is a measure for the efficiency of the stabilizer mixture. The values obtained are summarized in Table 3.

TABLE 3

| Stabilizer mixture | Time in hours until 0.1 carbonyl absorbance |
|---|---|
| 0.1% of (A-I-1) + 0.1% of (B-13) + 0.25% of anatase | 2715 |
| 0.1% of (A-II-1) + 0.1% of (B-13) + 0.25% of anatase | 3215 |
| 0.1% of (A-I-1) + 0.1% of (B-14) + 0.25% of anatase | 2755 |
| 0.1% of (A-II-1) + 0.1% of (B-14) + 0.25% of anatase | 3025 |
| 0.1% of (A-I-1) + 0.1% of (B-84-1-a) + 0.25% of anatase | 3035 |

EXAMPLE 4

Light Stabilization of Polyethylene HD Films 100 parts of unstabilized high density polyethylene powder (density: 0.964 g/cm$^3$; melt flow index; 5.0 g/10 min at 190° C. and 2160 g) are homogenized at 180° C. for 10 min in a Brabender plastograph with 0.03 parts of octadecyl 3-(3,5-di-tert-butyl-4-hydroxyphenyl)propionate, and the stabilizer mixture indicated in Table 4. The material thus obtained is compression molded in a laboratory press between two aluminum foils for 6 min at 210° C. to a 0.5 mm thick film which is cooled immediately to room temperature in a water-cooled press. Samples of 60 mm×25 mm are cut out of these 0.5 mm films and are exposed in a WEATHER-OMETER Ci 65 (black panel temperature 63±2° C., without water-spraying).

Periodically, these samples are removed from the exposure apparatus and their carbonyl content is measured with an infrared spectrophotometer. The exposure time corresponding to formation of a carbonyl absorbance of 0.1 is a measure for the efficiency of the stabilizer mixture. The values obtained are summarized in Table 4.

TABLE 4

| Stabilizer mixture | Time in hours until 0.1 carbonyl absorbance |
|---|---|
| 0.1% of (A-II-1) + 0.1% of (B-5-1) + 0.25% of anatase | 2995 |
| 0.1% of (A-II-1) + 0.1% of (B-97-II) + 0.25% of anatase | 2685 |
| 0.1% of (A-II-1) + 0.1% of (B-97-I) + 0.25% of anatase | 2265 |

What is claimed is:

1. A light stabilizer mixture containing (A) a compound of the formula

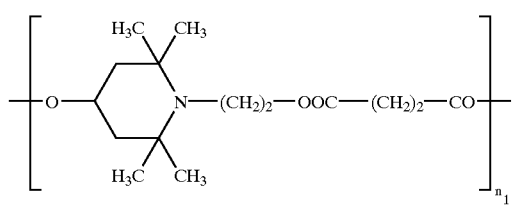

with $n_1$ being a number from 2 to 20, (B) a sterically hindered amine compound selected from the group consisting of

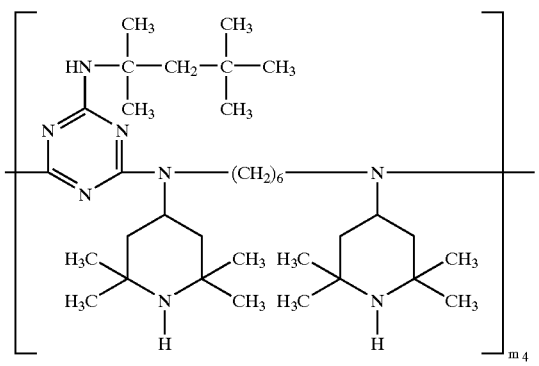

with $m_4$ being a number from 2 to 50;

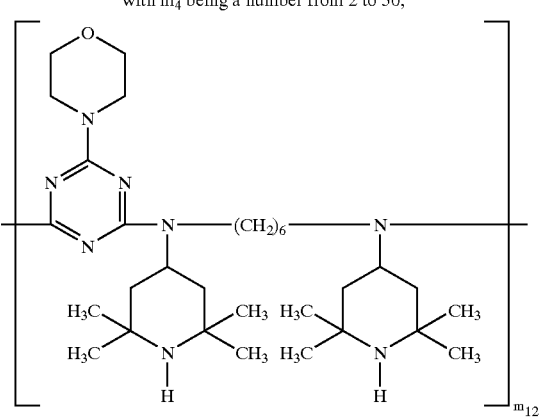

with $m_{12}$ being a number from 2 to 50;

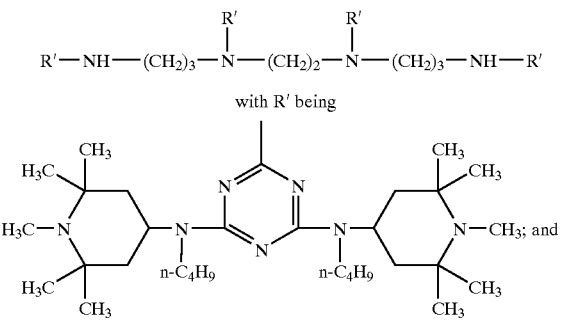

a product obtainable by reacting an intermediate product, obtained by reaction of a polyamine of the formula (100a-1) with cyanuric chloride, with a compound of the formula (100-1),

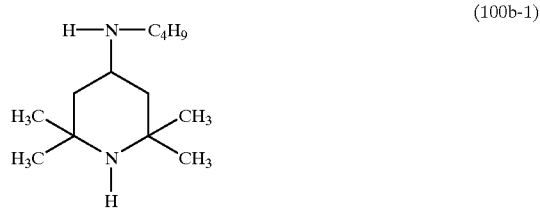

and (C) anatase;

with the proviso that the composition is essentially free of a halogenated hydrocarbyl phosphate or phosphonate ester flame retardant.

2. A light stabilizer mixture according to claim 1, wherein component (B) is a product represented by a compound of the formula (100-1-α), (100-2-α) or (100-3-α), or a mixture thereof
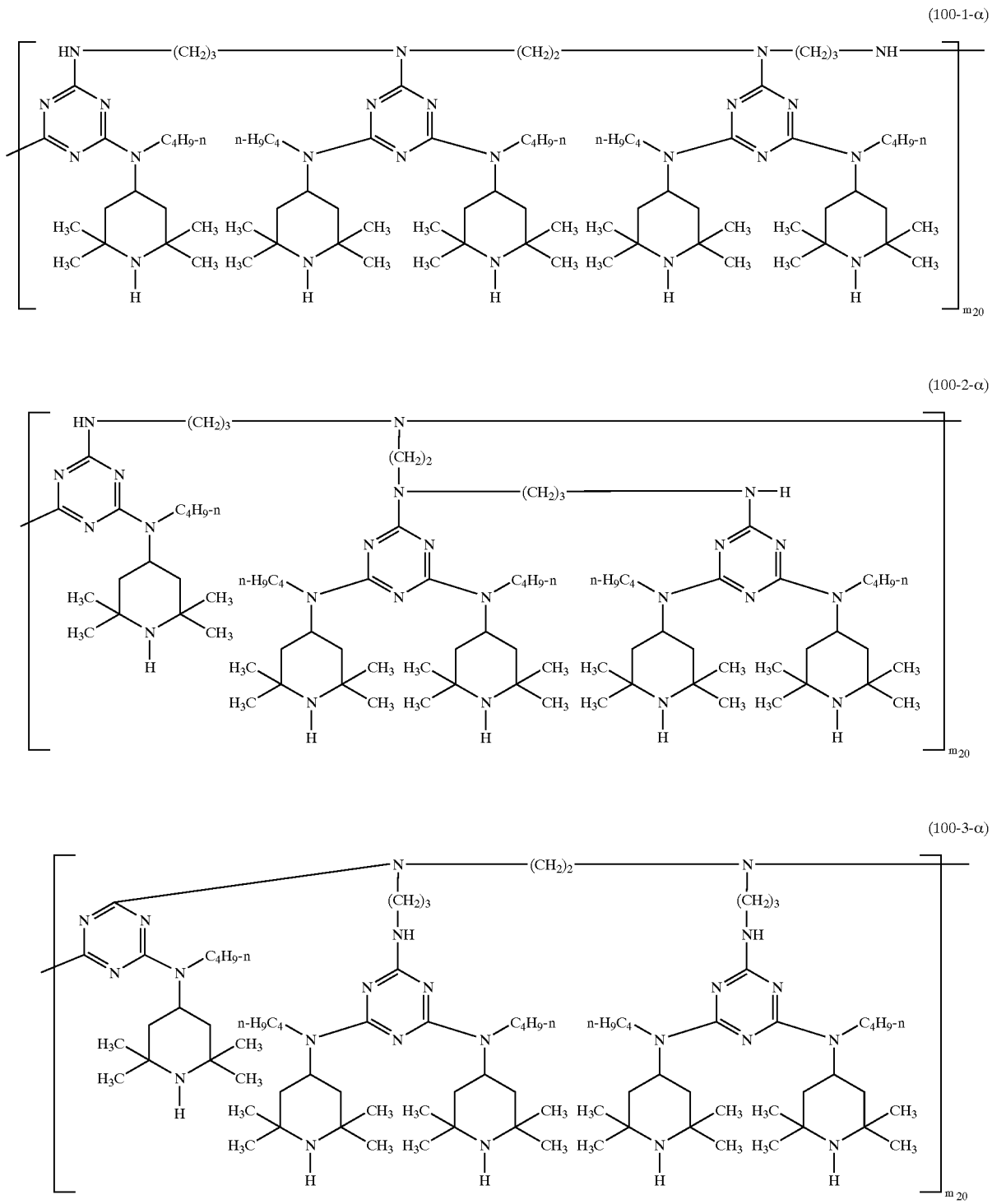
wherein $m_{20}$ is 2 to 20.

3. A light stabilizer mixture according to claim 1 wherein component (B) is a compound of the formula (100-3-α)

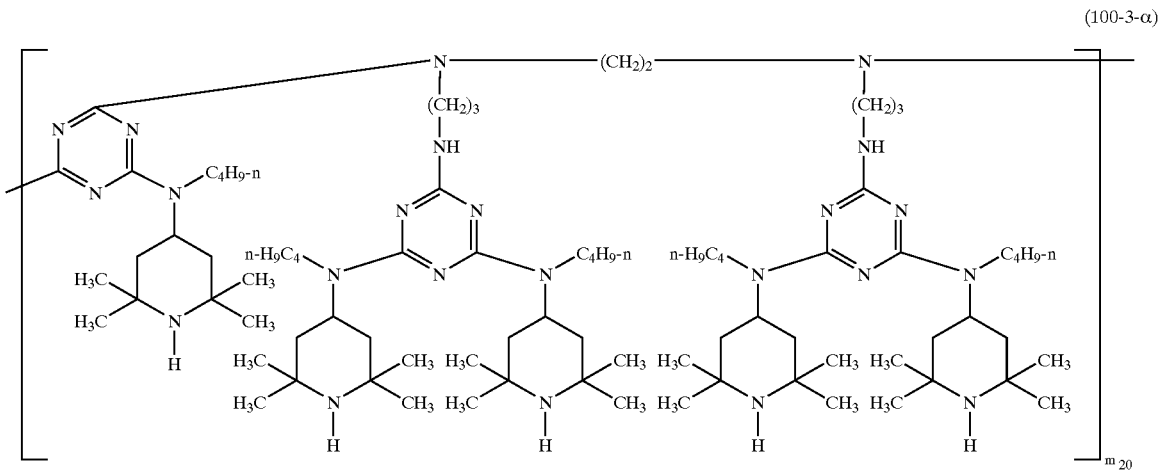

(100-3-α)

wherein $m_{20}$ is 2 to 20.

4. A light stabilizer mixture containing (A) a compound of the formula

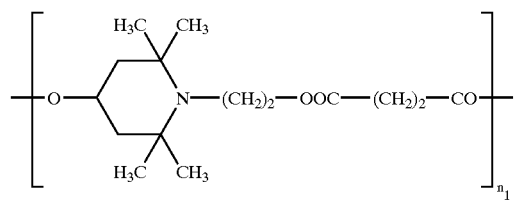

with $n_1$ being a number from 2 to 20, (B) a sterically hindered amine compound selected from the group consisting of

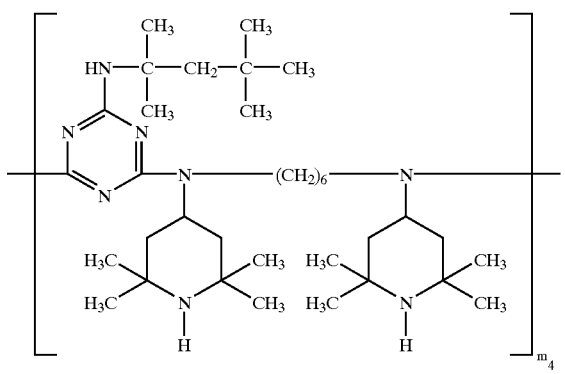

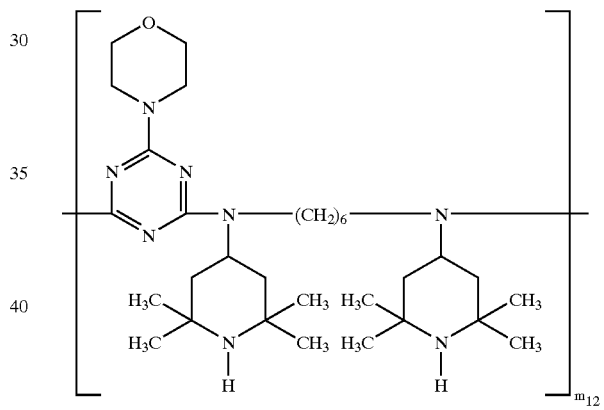

with $m_{12}$ being a number from 2 to 50;

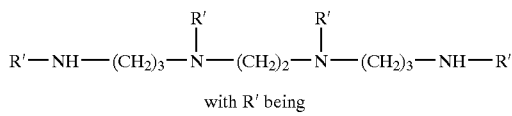

with R' being

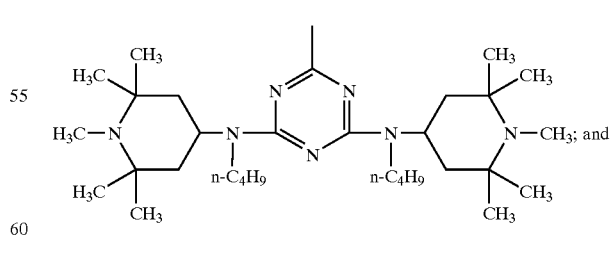

with $m_4$ being a number from 2 to 50;

a product obtainable by reacting an intermediate product, obtained by reaction of a polyamine of the formula (100a-1) with cyanuric chloride, with a compound of the formula (100b-1),

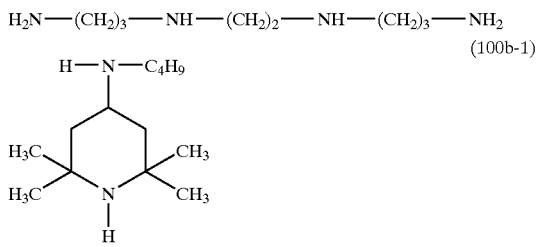

and (C) anatase;

with the proviso that the composition is essentially free of a flame retardant.

5. A light stablizer mixture according to claim 1 wherein the component (A)

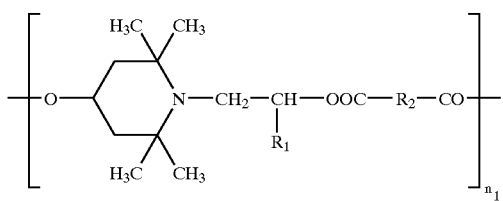

with $n_1$ being a number from 2 to 20, and

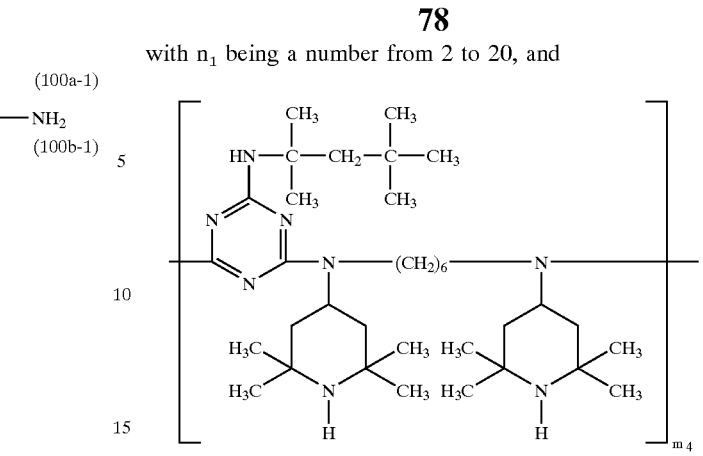

witn $m_4$ being a number from 2 to 50.

6. A composition comprising an organic material subject to degradation induced by light and a light stablizer mixture according to claim 1.

7. A composition according to claim 6 wherein the organic material is a synthetic polymer.

8. A composition according to claim 6 wherein the organic material is a polyolefin.

9. A composition according to claim 6 wherein the organic material is polyethylene, polypropylene, a polyethylene copolymer or a polypropylene copolymer.

10. A method for stablizing an organic material against degradation induced by light, which comprises incorporating into the organic material a light stablizer mixture according to claim 1.

* * * * *